United States Patent
Pal et al.

(10) Patent No.: US 9,968,780 B2
(45) Date of Patent: *May 15, 2018

(54) METHODS FOR USER CONTROL OF NEUROSTIMULATION TO MODIFY A COGNITIVE STATE

(71) Applicant: Thync Global, Inc., Los Gatos, CA (US)

(72) Inventors: Sumon K. Pal, Boston, MA (US); Jonathan Charlesworth, Menlo Park, CA (US); Anil Thakur, Fremont, CA (US); Isy Goldwasser, Los Gatos, CA (US); Daniel Z. Wetmore, Brooklyn, NY (US); Jason Egnal, Menlo Park, CA (US)

(73) Assignee: Thync Global, Inc., Los Gatos, CA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/210,742

(22) Filed: Jul. 14, 2016

(65) Prior Publication Data
US 2016/0317809 A1    Nov. 3, 2016

Related U.S. Application Data

(63) Continuation of application No. 14/634,551, filed on Feb. 27, 2015, now Pat. No. 9,399,126.
(Continued)

(51) Int. Cl.
*A61N 1/36* (2006.01)
*A61N 1/04* (2006.01)

(52) U.S. Cl.
CPC ....... *A61N 1/36025* (2013.01); *A61N 1/0456* (2013.01); *A61N 1/0476* (2013.01);
(Continued)

(58) Field of Classification Search
CPC . A61N 1/0476; A61N 1/0456; A61N 1/36025
See application file for complete search history.

(56) References Cited

U.S. PATENT DOCUMENTS

| | | | |
|---|---|---|---|
| 3,255,753 A | 6/1966 | Wing |
| 3,620,219 A | 11/1971 | Barker |
| (Continued) | | | |

FOREIGN PATENT DOCUMENTS

| | | |
|---|---|---|
| EP | 502919 B1 | 11/1993 |
| EP | 801957 A1 | 10/1997 |
| (Continued) | | |

OTHER PUBLICATIONS

Axelgaard Manufacturing Co. Ltd.; Little PALS® (product information); 2 pgs.; printed Feb. 11, 2013 from http://www.axelgaard.com/prod_little-pals.html.
(Continued)

*Primary Examiner* — Carl H Layno
*Assistant Examiner* — Jennifer Ghand
(74) *Attorney, Agent, or Firm* — Shay Glenn LLP

(57) ABSTRACT

Methods for allowing a user to control a neuromodulator to modify a cognitive state being experienced by the user. The user may select a waveform ensemble from a hand-held user device having an interface, and the user may adjust the perceived intensity of the applied waveform ensemble with the user device while the waveform ensemble is being applied. Also described are methods of managing communication between the hand-held user device (such as a smartphone or the like) and a wearable neurostimulator. Methods of displaying and visually tracking and controlling the applied waveform ensemble are also described herein.

20 Claims, 23 Drawing Sheets

Related U.S. Application Data

(60) Provisional application No. 61/945,135, filed on Feb. 27, 2014, provisional application No. 61/975,118, filed on Apr. 4, 2014, provisional application No. 61/994,860, filed on May 17, 2014, provisional application No. 62/002,860, filed on May 25, 2014, provisional application No. 62/099,960, filed on Jan. 5, 2015.

(52) U.S. Cl.
CPC ....... *A61N 1/0492* (2013.01); *A61N 1/36014* (2013.01); *A61N 1/0484* (2013.01)

(56) References Cited

U.S. PATENT DOCUMENTS

| | | |
|---|---|---|
| 3,648,708 A | 3/1972 | Haeri |
| 4,418,687 A | 12/1983 | Matsumoto et al. |
| 4,431,000 A | 2/1984 | Butler et al. |
| 4,646,744 A | 3/1987 | Capel |
| 4,664,117 A | 5/1987 | Beck |
| 5,144,952 A | 9/1992 | Frachet et al. |
| 5,183,041 A | 2/1993 | Toriu et al. |
| 5,335,657 A | 8/1994 | Terry et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,738,647 A | 4/1998 | Bernhard et al. |
| 5,792,067 A | 8/1998 | Karell |
| 6,066,163 A | 5/2000 | John |
| 6,280,454 B1 | 8/2001 | Wang |
| 6,324,432 B1 | 11/2001 | Rigaux et al. |
| 6,445,955 B1 | 9/2002 | Michelson et al. |
| 6,463,328 B1 | 10/2002 | John |
| 6,526,318 B1 | 2/2003 | Ansarinia |
| 6,567,702 B1 | 5/2003 | Nekhendzy et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,801,600 B1 | 9/2010 | Carbunaru et al. |
| 7,891,615 B2 | 2/2011 | Bevirt |
| 7,949,403 B2 | 5/2011 | Palermo et al. |
| 8,029,431 B2 | 10/2011 | Tononi |
| 8,086,318 B2 | 12/2011 | Strother et al. |
| 8,097,926 B2 | 1/2012 | De Graff et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egloff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,625 B2 | 7/2013 | Hargrove |
| 8,494,627 B2 | 7/2013 | Bikson et al. |
| 8,506,469 B2 | 8/2013 | Dietrich et al. |
| 8,532,758 B2 | 9/2013 | Silverstone |
| 8,560,075 B2 | 10/2013 | Covalin |
| 8,571,651 B2 | 10/2013 | Ben-Ezra et al. |
| 8,583,256 B2 | 11/2013 | Tracey et al. |
| 8,612,005 B2 | 12/2013 | Rezai et al. |
| 8,639,343 B2 | 1/2014 | De Vos |
| 8,660,644 B2 | 2/2014 | Jaax et al. |
| 8,688,239 B2 | 4/2014 | Hartlep et al. |
| 8,843,210 B2 | 9/2014 | Simon et al. |
| 8,874,219 B2 | 10/2014 | Trier et al. |
| 8,903,494 B2 | 12/2014 | Goldwasser et al. |
| 8,983,621 B2 | 3/2015 | Hou et al. |
| 9,002,458 B2 | 4/2015 | Pal et al. |
| 9,014,811 B2 | 4/2015 | Pal et al. |
| 9,067,054 B2 | 6/2015 | Simon et al. |
| 9,168,374 B2 | 10/2015 | Su |
| 9,205,258 B2 | 12/2015 | Simon et al. |
| 9,233,244 B2 | 1/2016 | Pal et al. |
| 9,248,292 B2 | 2/2016 | Trier et al. |
| 9,333,334 B2 | 5/2016 | Jeffery et al. |
| 9,364,674 B2 | 6/2016 | Cook et al. |
| 9,393,401 B2 | 7/2016 | Goldwasser et al. |
| 9,393,430 B2 | 7/2016 | Demers et al. |
| 9,399,126 B2 | 7/2016 | Pal et al. |
| 9,415,219 B2 | 8/2016 | Simon et al. |
| 9,440,070 B2 | 9/2016 | Goldwasser et al. |
| 9,446,242 B2 | 9/2016 | Griffith |
| 9,474,905 B2 | 10/2016 | Doan et al. |
| 9,656,076 B2 | 5/2017 | Trier et al. |
| 9,700,725 B2 | 7/2017 | Zhu |
| 9,731,116 B2 | 8/2017 | Chen |
| 9,744,347 B2 | 8/2017 | Chen et al. |
| 9,764,133 B2 | 9/2017 | Thomas et al. |
| 9,782,587 B2 | 10/2017 | Trier et al. |
| 2002/0116036 A1 | 8/2002 | Daignault et al. |
| 2003/0171685 A1 | 9/2003 | Lesser et al. |
| 2003/0225323 A1 | 12/2003 | Kiani et al. |
| 2004/0098065 A1 | 5/2004 | Hagglof et al. |
| 2004/0267333 A1 | 12/2004 | Kronberg |
| 2005/0165460 A1 | 7/2005 | Erfan |
| 2005/0267388 A1 | 12/2005 | Hanna |
| 2006/0064139 A1 | 3/2006 | Chung et al. |
| 2006/0149119 A1 | 7/2006 | Wang |
| 2006/0206163 A1 | 9/2006 | Wahlstrand et al. |
| 2007/0088419 A1 | 4/2007 | Fiorina et al. |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0045882 A1 | 2/2008 | Finsterwald |
| 2008/0132974 A1 | 6/2008 | Strother et al. |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2011/0029045 A1 | 2/2011 | Cevette et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |

(56) References Cited

U.S. PATENT DOCUMENTS

| | | |
|---|---|---|
| 2011/0276112 A1 | 11/2011 | Simon et al. |
| 2011/0288610 A1 | 11/2011 | Brocke |
| 2011/0301683 A1 | 12/2011 | Axelgaard |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0185020 A1 | 7/2012 | Simon et al. |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0302912 A1 | 11/2012 | Moffitt et al. |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2014/0031895 A1 | 1/2014 | Rahimi et al. |
| 2014/0128944 A1 | 5/2014 | Stern et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |
| 2014/0336728 A1 | 11/2014 | Franke et al. |
| 2015/0257970 A1 | 9/2015 | Mucke et al. |
| 2015/0328461 A1 | 11/2015 | Charlesworth et al. |
| 2015/0335877 A1 | 11/2015 | Jeffery et al. |
| 2015/0335888 A1 | 11/2015 | Demers et al. |
| 2016/0008632 A1 | 1/2016 | Wetmore et al. |
| 2016/0074657 A1 | 3/2016 | Kwan et al. |
| 2017/0076414 A1 | 3/2017 | Egnal et al. |
| 2017/0165470 A1 | 6/2017 | Jeffery |
| 2017/0182285 A1 | 6/2017 | Tyler et al. |
| 2017/0197081 A1 | 7/2017 | Charlesworth et al. |
| 2017/0224990 A1 | 8/2017 | Goldwasser et al. |
| 2017/0252562 A1 | 9/2017 | Goldwasser et al. |

FOREIGN PATENT DOCUMENTS

| | | |
|---|---|---|
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49-061984 A | 6/1974 |
| JP | 5-31197 A | 2/1993 |
| JP | 10-108913 A | 4/1998 |
| JP | 2002-306604 A | 10/2002 |
| JP | 2003-10230 A | 1/2003 |
| JP | 2006-192302 A | 7/2006 |
| JP | 3129187 U | 1/2007 |
| JP | 2009-85901 A | 4/2009 |
| JP | 2011-118293 A | 6/2011 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2015/061663 A1 | 4/2015 |
| WO | WO2015/143053 A1 | 9/2015 |

OTHER PUBLICATIONS

Axelgaard Manufacturing Co. Ltd.; PALS® Platinum Blue (product information); 2 pgs.; printed Feb. 11, 2013 from http://www.axelgaard.com/prod_pals-platinum-blue.html.

Chaieb et al.; Transcranial alternating current stimulation in the low kHz range increases motor cortex excitability; Restor Neurol Neurosci; 29(3); pp. 167-175; Mar. 2011.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feb. 2011.

GoFlow; tDCS Kit; product information; 9 pgs..; printed Feb. 10, 2014 (http://flowstateengaged.com/).

Gracenote; Timeline-metadata-api; 3 pages; retrieved from the Internet Jul. 7, 2015; (https://github.com/gracenote/timeline-metadata-api/blob/master/README.md).

Grindhouse Wetware; Thinking Cap; product information; 1 pg.; printed Feb. 10, 2014 (http://www.grindhousewetware.com/thinkingcap.html).

Kanai et al.; Frequency-dependent electrical stimulatioin of the visual cortex; Curr. Biol.; 18(23); pp. 1839-1843; Dec. 9, 2008.

Paulus, W.; Transcranial electrical stimulation (tES-tDCS; tRNS, tACS) methods; Neuropsychol Rehabil.; 21(5); pp. 602-617; Oct. 2011.

Prausnitz; The effects of electric current applied to skin: a review for transdermal drug delivery; Advanced Drug Delivery Reviews; vol. 18; pp. 395-425; Feb. 8, 1996.

Saiote et al.; High-frequency TRNS reduces BOLD activity during visuomotor learning; PLOS one; 8(3); e59669; 8 pgs.; Mar. 2013.

Schutter et al.; Brain oscillations and frequency-dependent modulation of cortical excitability; Brain Stimulation; 4(2); pp. 97-103; Apr. 2011.

STD Pharmaceutical Products; Idrostar intophoresis machine (product and use information); 9 pgs.; Dec. 2011 (printed Feb. 11, 2014 from http://www.iontophoresis.info/instructions/).

Terney et al.; Increasing human brain excitability by transcranial high-frequency random noise stimulation; The Journal of Neuroscience; 28(52); pp. 14127-14155; Dec. 2008.

Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filing date and any foreign priority date).

(56) References Cited

OTHER PUBLICATIONS

Tyler et al.; U.S. Appl. No. 61/550,334 entitled "Improvement Of Direct Communication," filed Oct. 21, 2011.
Tyler et al.; U.S. Appl. No. 61/663,409 entitled "Device And Methods For Noninvasive Neuromodulation Using Targeted Transcranial Electrical Stimulation," filed Jun. 22, 2012.
Jeffery et al.; U.S. Appl. No. 15/169,445 entitled "Methods and apparatuses for transdermal electrical stimulation," filed May 31, 2016.
Pal et al.; U.S. Appl. No. 15/170,878 entitled "Apparatuses and methods for neuromodulation," filed Jun. 1, 2016.
Aston-Jones et al.; An integrative theory of locus coeruleus-norepinephrine function: adaptive gain and optimal performance; Annu. Rev. Neurosci.; 28: pp. 403-450; Jul. 21, 2005.
Aston-Jones et al.; Role of locus coeruleus in attention and behavioral flexibility; Biological Psychiatry; 46(9); pp. 1309-1320; Nov. 1, 1999.
Backhaus et al.; Sleep disturbances are correlated with decreased morning awakening salivary cortisol; Psychoneuroendocrinology; 29(9): pp. 1184-1191; Oct. 31, 2004.
Basta et al.; Chronic Insomnia and the Stress System; Sleep Medicine Clinics; 2(2): pp. 279-291; (Author Manuscript, 20 pages); Jun. 30, 2007.
Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.
Berridge et al.; The locus coeruleus-noradrenergic system: modulation of behavioral state and state-dependent cognitive processes; Brain Research Reviews; 42(1); pp. 33-84; Apr. 30, 2003.
Brown et al.; Control of sleep and wakefulness; Physiological reviews; 92(3); pp. 1087-1187; Jul. 1, 2012.
Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.
Buchanan et al.; Salivary alpha-amylase levels as a biomarker of experienced fear; Communicative and Integrative Biology; 3(6); pp. 525-527; Nov. 1, 2010.
Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.
Buysse et al.; The Pittsburgh Sleep Quality Index: a new instrument for psychiatric practice and research; Psychiatric Research; 28(2); pp. 193-213; May 31, 1989.
Carter et al.; Tuning arousal with optogenetic modulation of locus coeruleus neurons; Nature Neuroscience; 13(12); pp. 1526-1533; Dec. 1, 2010.
Cook et al.; Trigeminal nerve stimulation in major depressive disorder: acute outcomes in an open pilot study; Epilepsy and Behavior; 28(2): pp. 221-226; Aug. 31, 2013.
Degiorgio et al., Trigeminal nerve stimulation for epilepsy: long-term feasibility and efficacy; Neurology; 72(10): pp. 936-938; Mar. 10, 2009.
Degiorgio et al.; Randomized controlled trial of trigeminal nerve stimulation for drug-resistant epilepsy; Neurology; 80(9); pp. 786-791; Feb. 26, 2013.
Elder et al.; The cortisol awakening response—applications and implications for sleep medicine; Sleep Medicine Reviews; 18(3): pp. 215-224; Jun. 30, 2014.
Eschenko et al.; Noradrenergic neurons of the locus coeruleus are phase locked to cortical up-down states during sleep; Cerebral Cortex; 22(2); pp. 426-435; Feb. 1, 2012.
Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.

Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
Golestanirad et al; Analysis of fractal electrodes for efficient neural stimulation; Frontiers in Neuroengineering; 6(3); 10 pages; Jul. 2013.
Granger et al.; Salivary alpha-amylase in biobehavioral research: recent developments and applications; Annals of the New York Academy of Sciences; 1098(1); pp. 122-144; Mar. 1, 2007.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Just et al.; Bold responses to trigeminal nerve stimulation; Magnetic Resonance Imaging; 28(8): pp. 1143-1151; Oct. 31, 2010.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441(7093): pp. 589-594; Jun. 1, 2006.
Magis et al.; Safety and patients' satisfaction of transcutaneous supraorbital neurostimulation (tSNS) with the Cefaly (R) device in headache treatment: a survey of 2,313 headache sufferers in the general population; The Journal of Headache and Pain, 14(1); pp. 95; (manuscript version, 8 pages) Dec. 1, 2013.
Meltzer et al; Direct comparison of two new actigraphs and polysomnography in children and adolescents; Sleep; 35(1); pp. 159-166; Jan. 1, 2012.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-160; Apr. 30, 2001.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico- motoneuronal excitability by the selective norepinephrine reuptake inhibitor reboxetine; Neuroscience Letters; 330(3); pp. 231-234; Sep. 27, 2002.
Pusch et al.; Electrical stimulation of the vestibular system prevents postoperative nausea and vomiting; Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.

(56) References Cited

OTHER PUBLICATIONS

Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking. Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7(6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; Jan. 1, 2015.
Trevizol et al.; Trigeminal Nerve Stimulation (TNS) for Post-traumatic Stress Disorder: A Case Study; Brain Stimulation; 8(3): pp. 676-678; Jan. 1, 2015.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3); pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.
Pal et al.; U.S. Appl. No. 14/956,193 entitled "Transdermal electrical stimulation devices for modifying or inducing cognitive state," filed Dec. 1, 2015.
Tyler et al.; U.S. Appl. No. 15/536,148 entitled "Methods and apparatuses for transdermal stimulation of the outer ear," filed Jun. 15, 2017.
Tyler et al.; U.S. Appl. No. 15/536,151 entitled "Systems and methods for transdermal electrical stimulation to improve sleep," filed Jun. 15, 2017.

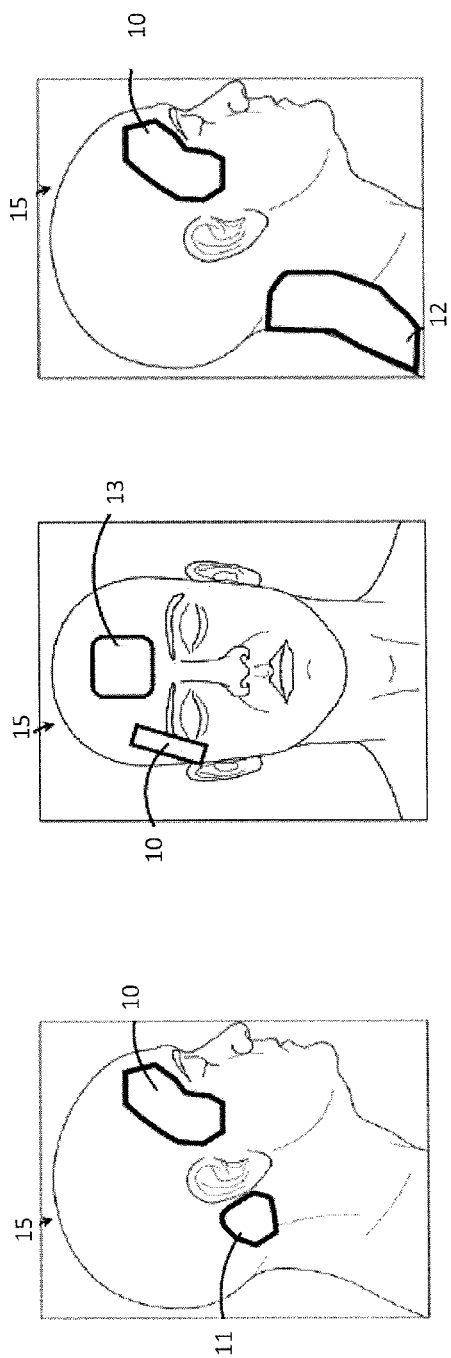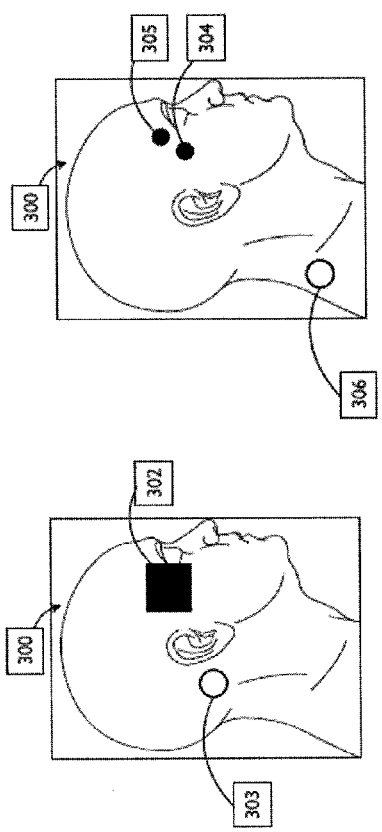

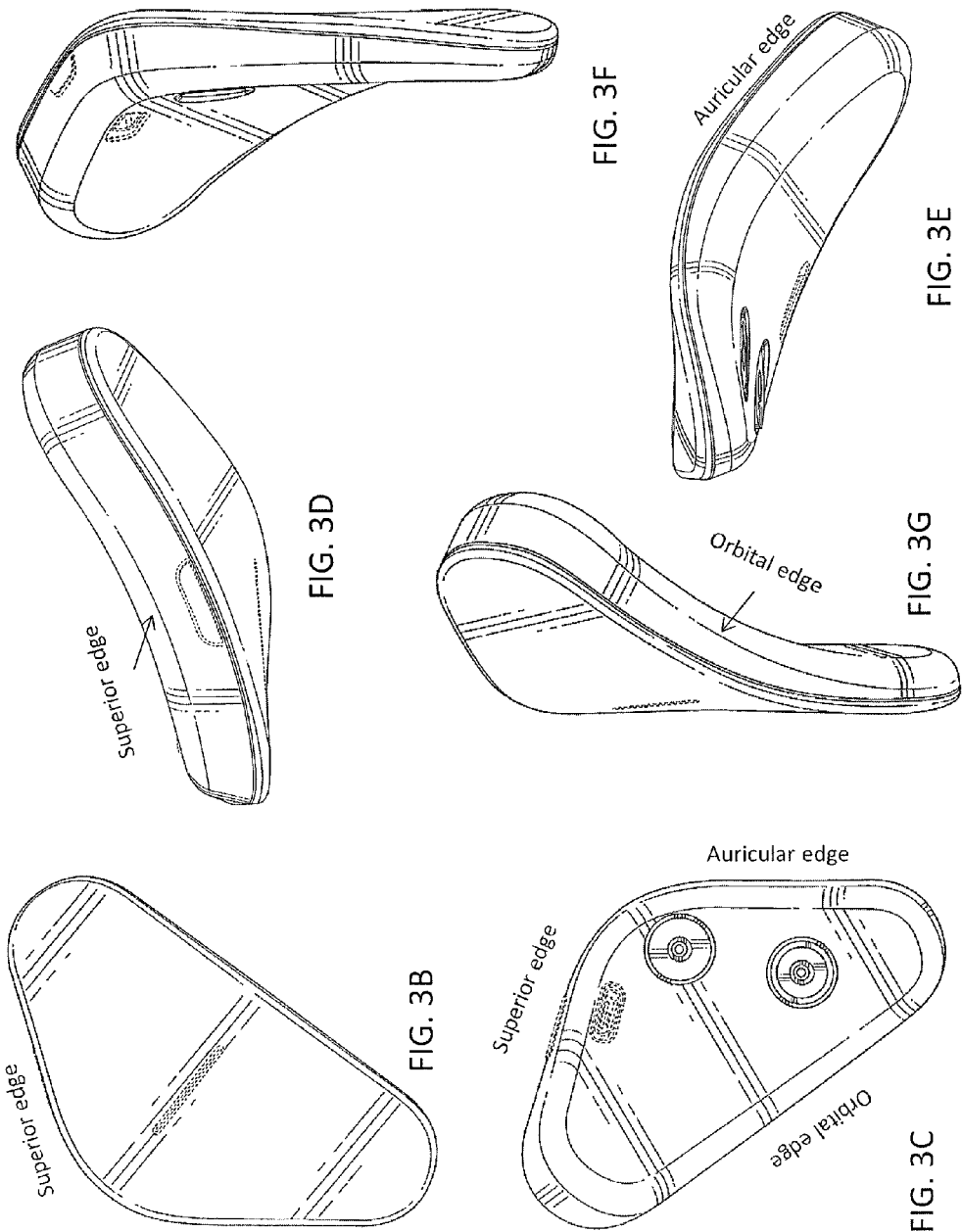

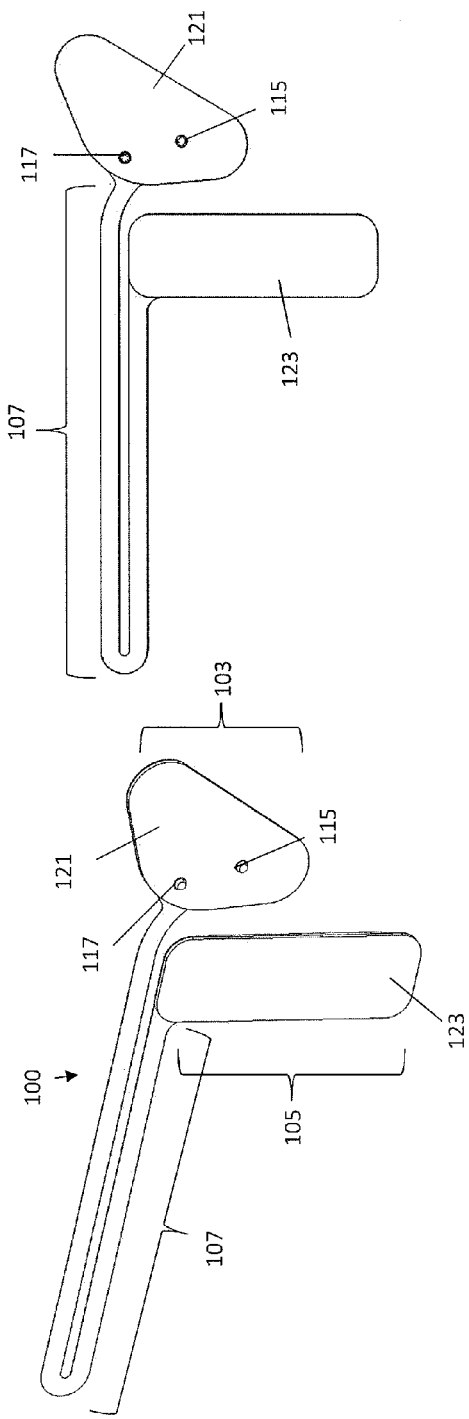
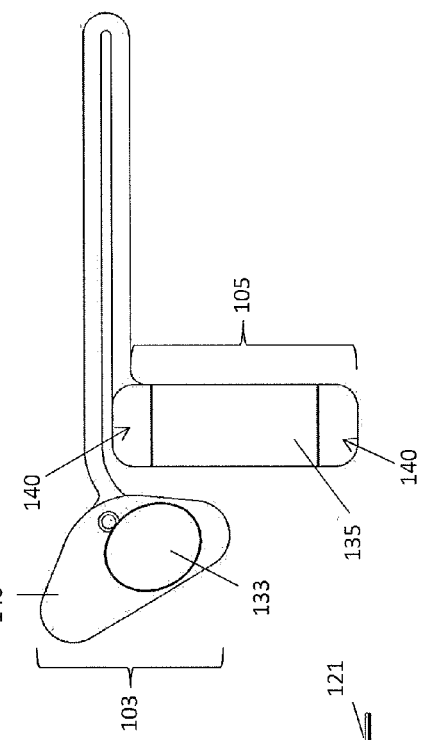
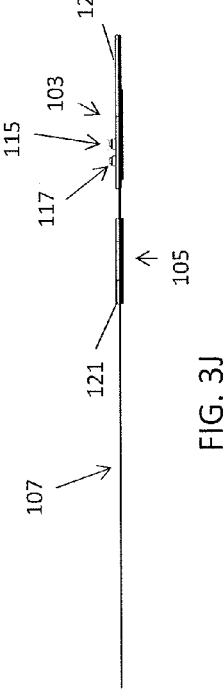
FIG. 3H
FIG. 3I
FIG. 3J
FIG. 3K

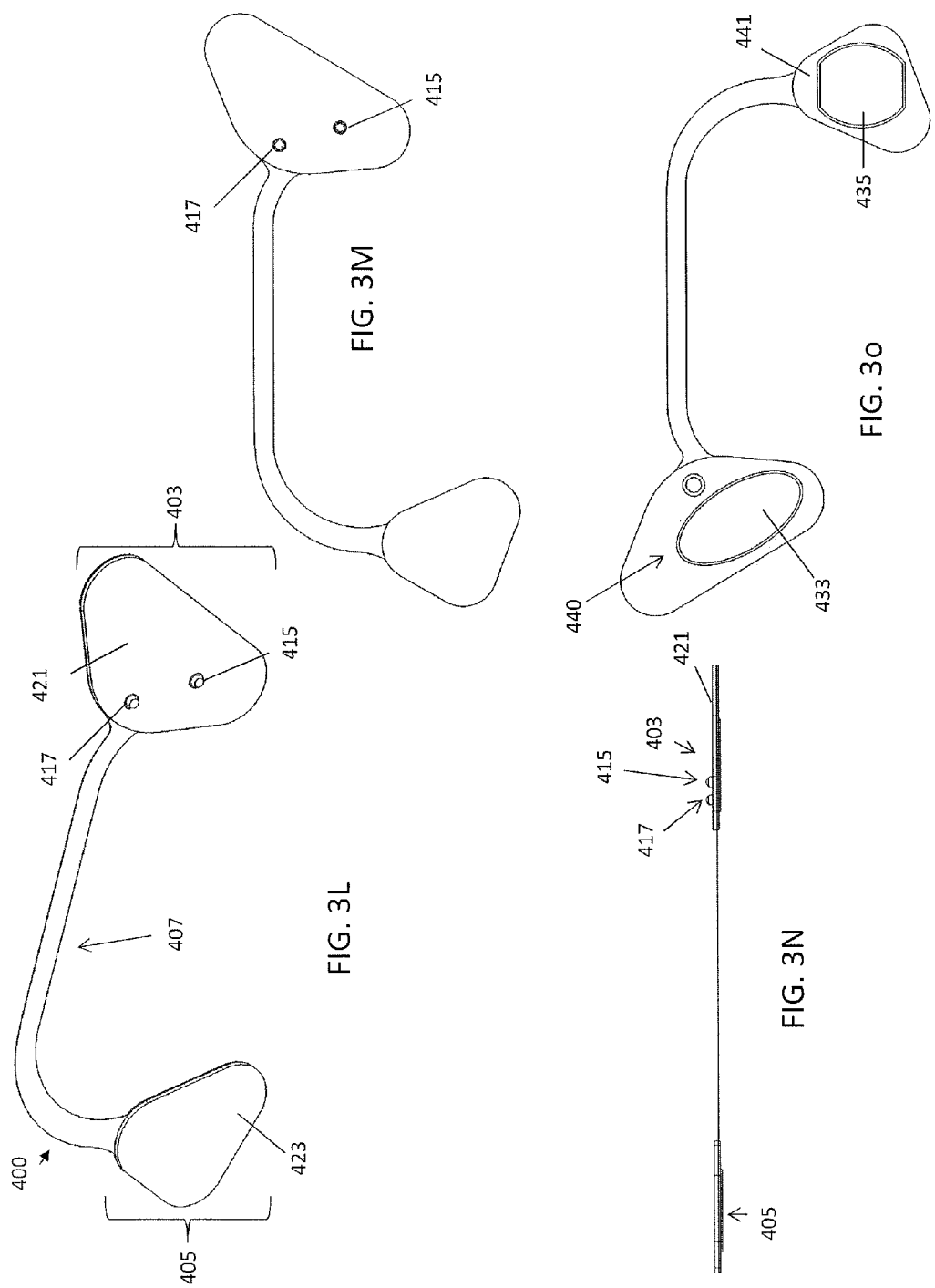

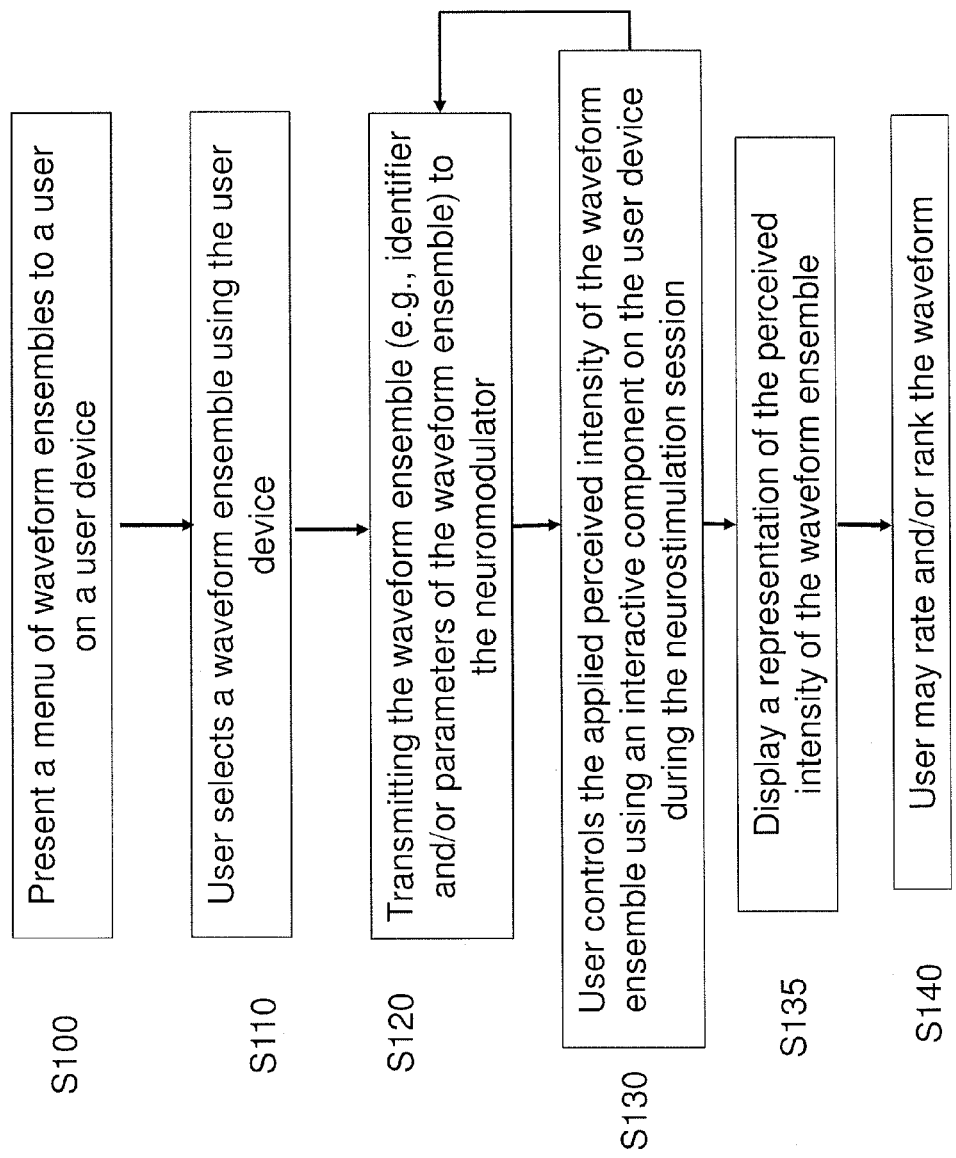

METHODS FOR USER CONTROL OF NEUROSTIMULATION TO MODIFY A COGNITIVE STATE

CROSS REFERENCE TO RELATED APPLICATIONS

This patent application is a continuation of U.S. patent application Ser. No. 14/634,551, titled "METHODS FOR USER CONTROL OF NEUROSTIMULATION TO MODIFY A COGNITIVE STATE," filed Feb. 27, 2015, now U.S. Pat. No. 9,399,126, which claims priority to each of the following U.S. provisional patent applications: U.S. Provisional Patent Application No. 61/945,135, titled "TRANSDERMAL ELECTRICAL STIMULATION SYSTEMS FOR INDUCING PHOSPHENES," filed on Feb. 27, 2014; U.S. Provisional Patent Application No. 61/975,118, titled "TRANSDERMAL ELECTRICAL STIMULATION SYSTEMS," filed on Apr. 4, 2014; U.S. Provisional Patent Application No. 61/994,860, titled "SYSTEMS, DEVICES, AND METHODS FOR TRANSDERMAL ELECTRICAL STIMULATION WAVEFORM DESIGN AND USE," filed May 17, 2014; U.S. Provisional Patent Application No. 62/002,860, titled "TRANSDERMAL ELECTRICAL STIMULATION SYSTEMS FOR INDUCING COGNITIVE EFFECTS AND METHODS OF USING THEM," filed on May 25, 2014; and U.S. Provisional Patent Application No. 62/099,960, titled "METHODS AND APPARATUSES FOR USER CONTROL OF NEUROSTIMULATION," filed on Jan. 5, 2015. Each of these applications is herein incorporated by reference in its entirety.

This patent application may also be related to the following U.S. patent applications, which are herein incorporated by reference in their entirety: U.S. application Ser. No. 14/320,443, titled "TRANSDERMAL ELECTRICAL STIMULATION METHODS FOR MODIFYING OR INDUCING COGNITIVE STATE," filed on Jun. 30, 2014, now U.S. Pat. No. 9,014,811, and U.S. patent application Ser. No. 14/558,604, titled "WEARABLE TRANSDERMAL ELECTRICAL STIMULATION DEVICES AND METHODS OF USING THEM", filed on Dec. 2, 2014, now U.S. Pat. No. 9,440,070.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates generally to neuromodulation, and more specifically to methods and apparatuses for user control of neurostimulation and neurostimulation waveforms.

BACKGROUND

The brain is composed of neurons and other cell types in connected networks that process sensory inputs, generate motor commands, and control all other behavioral and cognitive functions. Neurons communicate primarily through electrochemical pulses that transmit signals between connected cells within and between brain areas. Noninvasive neuromodulation technologies that affect neuronal activity can modulate the pattern of neural activity and cause altered behavior, cognitive states, perception, and motor output without requiring an invasive procedure.

Transcranial/transdermal electric stimulation (hereinafter "TES") through scalp electrodes has been used to affect brain function in humans. TES has been shown to improve motor control and motor learning, improve memory consolidation during slow-wave sleep, regulate decision-making and risk assessment, affect sensory perception, and cause movements. TES has been used therapeutically in various clinical applications, including treatment of pain, depression, epilepsy, and tinnitus. Despite the research to date on TES neurostimulation, existing methods and apparatuses for TES are lacking the capability of allowing the user to control the neurostimulation sessions.

Most electrical stimulation systems targeting the nervous system incorporate a tabletop or handheld piece of hardware comprising a user interface, electrical control circuitry, a power supply (e.g. battery), wires leading to electrodes affixed to a user, and predetermined and/or preconfigured electrical stimulation protocols. Available systems are limited regarding to the perspective of allowing the user to select and run the TES waveforms. Moreover, available systems do not permit the user to adjust the predetermined/preconfigured electrical stimulation protocol.

Existing neuromodulation devices and/or systems (e.g. TES systems) are not typically equipped with a user interface for allowing a user to select and run the TES waveforms, to adjust and/or control the TES waveforms, and share the TES waveforms with other users. Methods and apparatuses for allowing the user to control a TES neurostimulator would be advantageous. Furthermore, a user device, such as a handheld computing device (e.g., smartphone, tablet, laptop, etc.) that is configured to enable a user to select and adjust the perceived intensity of, in real- or near-real time, stimulation parameters, and particularly the complex stimulation waveforms such as ensemble waveforms having a variety (e.g., 3 or more) of stimulation episodes that are adapted to evoke a particular cognitive effect, would be advantageous. Such systems may allow a high level of efficacy, comfort, and convenience. Methods and apparatuses for controlling a TES session would be advantageous for self-actuated systems for use in everyday settings.

Thus, there is a need for new and useful methods and apparatuses for allowing the user to control the transdermal electrical stimulation waveforms of the neurostimulator. This invention provides such new and useful methods and apparatuses.

SUMMARY OF THE DISCLOSURE

Described herein are methods and apparatuses for allowing a user receiving neurostimulation to select a particular neurostimulation treatment from a menu of such treatments ("ensemble waveforms"), which may be organized by intended cognitive effect, and may include ranking and/or rating (i.e. scoring) information, and to control the intensity (e.g., increasing or decreasing the perceived intensity) of the treatment, and in some cases adding effects to an ongoing treatment, such as evoking phosphenes, or to extend a currently running waveform.

In general, the methods and apparatuses described herein include methods of allowing the user to control the neurostimulator to evoke a particular cognitive effect by selecting and applying a neurostimulation waveform ensemble from a menu of ranked and/or sorted waveform ensembles. The waveform ensemble may be a composition of transdermal electrical stimulation waveforms. The waveform ensemble may induce a strong and reliable cognitive effect while mitigating skin irritation, pain, and tissue damage. Waveforms may be defined according to one or more of: frequency, peak intensity, duty cycle, the proportion of nonzero current flow that is positive-going (i.e. 'percent direct current'), whether the waveform is biphasic, charge imbalanced, includes a capacitive discharge component, etc. The waveform ensembles may be applied continuously or intermittently. The overall cognitive effects perceived by the user (including effects experienced as skin sensations) can be indicated by the perceived intensity of the waveform ensemble which will be discussed in detail below. Perceived intensity may refer to the effect that the intensity has on the user experience. For example, when changing the intensity (e.g., modifying one or more of frequency, current amplitude, duty cycle, etc.), the user may experience a change in perceived intensity in one or more ways, e.g., as a change in perceived skin sensation, change in subjectively experienced cognitive effect, change in physiological muscle response (e.g., muscle tightness or twitching of eyelid muscle), or the like.

In general, described herein are methods of allowing the user to modify a cognitive state. The method can comprise presenting a plurality of waveform ensembles to a user with a user device. The user device may be configured to interact with the user and allow user control as described herein. For example, the user device may be configured using software, hardware, firmware, or the like, including combinations of these, for example, by executing an "application" or "app" that controls a processor of the user device to perform the methods describe herein. In general, a user device may include a handheld device having a processor and/or controller (e.g. microcontroller), including, for example, a smartphone (e.g., iPhone, Android-type phone, etc.), tablet (iPad, etc.), wearable electronics (e.g., Google glass, smartwatch, etc.) or the like, including custom/dedicated devices. The methods described herein may include allowing the user to download an application into a user devices. A user device may also be referred to herein as a user computing device. The user device may include a display, a processor, and one or more inputs (which may include a touchscreen), as well as a wireless communication module for wirelessly pairing and communicating with the neurostimulator device worn by the user (e.g., Bluetooth, near field communication, etc.) and/or with an electrode assembly worn by the user.

In general, the application may allow the user to view a library of waveform ensembles which can be applied by the neurostimulator to induce cognitive effects. The methods and apparatuses described herein may be configured to allow the user to select a waveform ensemble from the plurality of waveform ensembles with a user interface on the user device. The method may include transmitting the waveform ensemble to a neurostimulator worn on the user's head. The method may further include applying the waveform ensemble from the neurostimulator to modify the user's cognitive state. The neurostimulation may be triggered by the user using the user computing device that wirelessly communicates with the neurostimulator applied to the user's head. The user may activate the operation of the TES himself or herself. For example, activating the neurostimulator may include wirelessly triggering activation of the neurostimulator by the user through the user interface of the application.

For example, described herein are methods of allowing a user to modify a cognitive state that include: allowing the user to select a waveform ensemble from a plurality of waveform ensembles on a user device; transmitting either an identifier of the selected waveform ensemble, or waveform parameters for the waveform ensemble (or both) to a neurostimulator worn on the user's head for application of the waveform ensemble; and allowing the user to adjust the perceived intensity of the applied waveform ensemble with the user device during application of the waveform ensemble.

As used herein a waveform ensemble typically includes a family of sets of waveform parameters (where the set of waveform parameters may specify current intensity, frequency, duty cycle, and percent charge imbalance, and optionally, capacitive discharge and amplitude modulation) that together define a stimulation protocol having a plurality of different waveform parameters that are arranged sequentially, and may include a duration for each set. For example, an ensemble waveform may include a series of 3 or more (e.g., 4 or more, 5 or more, 6 or more, 7 or more, 8 or more, 9 or more, 10 or more, etc.) component waveforms, wherein all or some of the component waveform is biphasic and has a duration and a predefined set of waveform parameters including a frequency, an intensity, a duty cycle and a percent charge imbalance, wherein at least one of the waveform parameters of each component waveform is different from the waveform parameters of a component waveform preceding it, following it, or preceding and following it in the series. Functionally, a waveform ensemble may be created to evoke a particular cognitive effect, such as relaxation, calmness, energy, etc. Examples of waveform ensembles are described herein.

For example, any of the methods of allowing a user to modify a cognitive state described herein may include: presenting a plurality of waveform ensembles to a user with a user device (e.g., a computing device); allowing the user to select a waveform ensemble from the plurality of waveform ensembles; transmitting the waveform ensemble, an identifier of the waveform ensemble, and/or a waveform parameter of the waveform ensemble to a neurostimulator worn on the user's head; applying the waveform ensemble from the neurostimulator to modify the user's cognitive state; and allowing the user to adjust the perceived intensity of the applied waveform ensemble with the user device during application of the waveform ensemble.

As used herein, the perceived intensity of the applied waveform ensemble is perception of the stimulation, e.g., both cognitive perception of the intended cognitive effect, such as calmness or energy, and/or the perception of the electrode and applied stimulation on the subject's skin, such as tingling, burning, itching, "pins and needles", muscle twitching or tightening, and the like. The perceived intensity may be adjusted by, for example, modifying one or more of the peak intensity (e.g., increasing or decreasing the peak applied current) applied by the neurostimulator, the frequency of the applied current (e.g., typically increasing the applied frequency to reduce the perceived intensity, decreasing the applied frequency to increase the perceived intensity), applying a capacitive discharge to some or all of the pulses within the applied waveform (also referred to as applying "short circuiting" pulses, which typically reduces the perceived intensity of the waveform), increasing or decreasing the duty cycle (typically increasing the duty cycle increases the perceived intensity), and increasing or decreasing the percent charge imbalance (typically increasing the percent charge imbalance will increase the perceived intensity). Stimulating at a higher frequency may cause lower skin sensations, and may actually be better for inducing a cognitive effect.

As mentioned, any of these methods may allow the user to select from a subset of waveform ensembles that are configured to evoke a type of cognitive state. A group or list of waveform ensembles may include waveform ensembles that are configured to evoke different cognitive effects, such as invoking "calm" (e.g., enhancing relaxation, calming, mental clarity, peace, introspection, facilitating the induction of or improving the quality of sleep, or the like), or invoking "energy" (e.g., generally evoking a feeling of energy, enhancing focus and attention; enhancing alertness; increasing focus and/or attention; enhancing wakefulness; increasing subjective feeling of energy; increasing objective psychophysiological energy levels; increasing motivation; increasing psychophysiological arousal; and evoking a physical sensation of warmth in the subject's chest).

Thus, the waveforms may be grouped based on the evoked effect (broadly, calm and energy) and within these broader groups into sub-groups by other qualifiers, such as degree of effect, duration of the session (ensemble waveform), ranking or scoring, persistence of the effect, etc. The user may then manually select from one or more of these categories, which may be presented as menus or the like on the user device, or an automated selection may be made from the list based on user experience, user preferences, user demographic data, etc.

In some variations, the user device may be in communication with the electrode assembly and may automatically detect when the electrode assembly and neurostimulator are attached (and/or are making sufficient contact with a user's skin). This information may be presented on the user device and/or may be used to help guide the user in selecting the waveform ensemble to use. In some variations, the type or category of waveform ensemble (e.g., the desired cognitive effect, such as calm or energy) may depend on the electrode type and/or placement of the electrodes on the user. Thus, in some variations the apparatus may communicate with the electrode assembly to confirm the type of electrode assembly (e.g., a 'calm' electrode assembly configuration, adapted to be worn on the user's temple and neck, or an 'energy' electrode assembly configuration, adapted to be worn on the user's temple and mastoid region). When the user computing device (handheld device) confirms a particular type of electrode assembly, the user may be presented with the sub-set of waveform ensembles that are relevant to that type of electrode assembly (e.g., calm, energy, etc.), and other waveform ensembles may be hidden, de-activated, or shaded out, etc.

Thus, in some variations the neurostimulator may send a signal to the user device indicating that an electrode has been attached to the neurostimulator, and/or what type of electrode has been attached. In some variations, the neurostimulator (and/or the electrode assembly) may communicate with the user device controlling the electrode assembly additional information about the electrode assembly, such as batch and/or manufacturing data; sizing information (e.g. for heads of different sizes or shapes); information about previous use of a reusable electrode; capacity information (i.e. how much stimulation with particular charge imbalance parameters can be delivered comfortably, without using up pH-buffering consumable components of an electrode); etc.

The user may also be permitted to rank, tag, rate, or score any of the waveform ensembles, e.g., after experiencing them, or to view ranks, tags (e.g., descriptions), ratings, and/or scores made by other users. For example, in some variations, the user may be permitted or invited to rank or score a waveform ensemble in the plurality of waveform ensembles, and the user device or system may then store, transmit, or store and transmit the user's rank or score for that waveform ensemble. In some variation, the method may also include storing, transmitting, or storing and transmitting the intensity adjustments (e.g., adjustment to the perceived intensity) made by the user when playing the waveform ensemble, including the timepoints during a waveform when the intensity adjustments were made. When the method permits or requests user ranking or scoring, the ranking may be based on a user providing a rating; in some variations the rating may be generated as an efficacy rating that is determined automatically or algorithmically by measurement of user physiology (which may include brain recording, heart rate, GSR, etc.) or cognitive assessment, rather than or in addition to user self-reporting.

In general, any of the methods described herein may also include a step of the user downloading or acquiring additional (e.g., new) waveform ensembles onto the user device. For example, waveform ensembles may be acquired from a remote server (e.g., downloaded from an Internet site, shop, forum, or marketplace), or may be generated by a user and/or shared from other users.

In any of the methods described herein the user device may display a rank or score for the waveform ensemble, which may be useful or helpful for the user when selecting which waveforms to use. Further the ranking may be done as part of a review by a skilled practitioner of TES which may be provided (or a link provided thereto).

In any of the variations described herein, the user may trigger a predetermined effect from the user device while the neurostimulator is applying an ensemble waveform. The predetermined effect may suspend, interrupt, or modify the ongoing ensemble waveform in order to perform the predetermined effect. For example, a user may be permitted to trigger (e.g., by activating a control on the user device, such as pushing a button from a touchscreen on the device), from the user device, transmission of an interrupt signal to the neurostimulator during the application of the waveform ensemble, wherein the interrupt signal temporarily modifies the application of the waveform ensemble for a predefined timer period. Examples of predetermined effects are described herein, but typically include a brief (e.g., less than a few seconds, less than 3 sec, less than 4 sec, less than 5 sec, less than 6 sec, less than 7 sec, less than 8 sec, less than 9 sec, less than 10 sec, less than 20 sec, etc.) waveform or modification of the currently running waveform ensemble, such as a temporary decrease in the perceived intensity followed by an increase in the perceived intensity (e.g., by adjusting one or more of frequency, current amplitude, duty cycle, percent charge imbalance, etc.), or a waveform configured to evoke a phosphene in the user. A predetermined effect may be available for triggering at restricted timepoints during an ensemble waveform (i.e. so that the comfort and efficacy of the predetermined effect are likely to be high).

For example, the method may include allowing the user to trigger, from the user device, transmission of an interrupt signal to the neurostimulator during the application of the waveform ensemble, wherein the interrupt signal temporarily modifies the application of the waveform ensemble for a predefined timer period, and wherein the interrupt signal is configured to evoke phosphenes. For example, in some variations the user may trigger, from the user device, transmission of an interrupt signal to the neurostimulator during the application of the waveform ensemble, wherein the interrupt signal temporarily modifies the application of the waveform ensemble for a predefined timer period, wherein the interrupt signal is configured to transiently decrease and then increase (or alternatively, transiently increase and then decrease) the perceived intensity of the waveform ensemble.

The user device may also be configured to provide help to the user in operating the system and/or in applying the device, e.g., electrode(s) and neurostimulator, on the subject's head in the correct positions. For example, any of the methods described herein may also include displaying, on the user device, a video including instructions for use of the neurostimulator. In some variations the method (and an apparatus configured to perform it) may be configured to allow the user to confirm the position of the neurostimulator by displaying in real-time images from a camera on the user device so that the user may view an image of the user's head. Note that "real time" may refer to approximately real time, as there may be some necessary delay due to signal transmission and processing time (e.g., approximately real time may mean within less than about a 1 sec delay).

Any of the methods and apparatuses described herein may include tracking the user's use of the apparatus and/or the number of electrodes that the user has. Since electrodes may be disposable and/or single- or low-number count use electrodes, the method and/or apparatus may automatically ship a user electrodes (e.g., energy, calm, etc. electrodes) based on usage and/or based on the passage of time. For example, a user may initially set up a number of electrode assemblies to have shipped and a threshold for shipping additional electrode assemblies based on time (i.e. monthly subscription) and/or use (i.e. once a user has used five electrode assemblies from a previous shipment). For example the user may set up (e.g., on the user device and/or a remote server) to ship their predetermined number of electrode assemblies (e.g., 5 electrodes) after a set condition is met (e.g., any time the user has less than 3 electrodes). The number and types of electrodes to send, billing information, shipping preferences, and triggering conditions may be set by the user initially (e.g., including the initial number of electrodes which may alternatively be presumed to be 1, zero, or the number in a "starter kit"). The electrode assemblies to be shipped may be electrode sets or cantilevered electrodes, including any of the electrodes described herein including electrode assemblies with multiple active areas. In some variations, the apparatuses (e.g., control logic controlling a user device, etc.) may estimate or calculate a tally of the number of electrodes that the user has, or is expected to have, based on the operation of the system (historic information on use), an updated count of electrodes provided by the user via the user interface of the user device, and/or communication with the user (e.g. by sending a text, email, or other communication). Thus, any of these methods or apparatuses may include automatically estimating the number of electrodes the user has and prompting, on the user device, a request to purchase additional electrodes.

In general, any of the apparatuses and methods described herein may track the user's operation of the neurostimulator(s), e.g., by tracking the use of the control logic running on a user device. This tracking may be centralized, e.g., on a remote ("cloud") server, or it may be local to the user device and/or neurostimulator. For example, the apparatus (e.g., control software and/or circuitry), may track the application of waveform ensembles by the user, including the types of waveform ensembles, user adjustments to the perceived intensity during delivery of the ensemble waveform, and any ratings, rankings, scores, or comments from the user regarding the waveform ensembles. Tracking may optionally include any of: measuring, e.g., measuring the adjusted perceived intensity; storing values to a memory, e.g., on the user device and/or neurostimulator; and transmitting the value to a controller device or to a remote server, e.g., via the Internet.

In general, presenting the plurality of waveform ensembles may comprise indicating historical use information for each waveform ensemble in the plurality of waveform ensembles, which may include user adjustments to the perceived intensity of the waveform.

Presenting the plurality of waveform ensembles may include indicating ranking, rating, tagging, or scoring information for individual waveform ensembles in the plurality of waveform ensembles based on ranks, ratings, tags or scores made by other users. In some variations, presenting the plurality of waveform ensembles may include indicating ranking or scoring information for individual waveform ensembles in the plurality of waveform ensembles based on ranks, tags, ratings, or scores made by the user. Ranking, tagging, rating, or scoring information may be included as a description that is annotated with the name, duration, date of release, or other descriptive information about each waveform ensemble, if available.

Also described herein are apparatuses for performing any of the methods described herein, which include software, firmware, and/or hardware (or combinations thereof). For example, also described herein are software which may be described as a non-transitory, computer-readable storage medium storing a set of instructions capable of being executed by a processor to control the operation of a neurostimulator worn by a user, and that when executed by the processor, causes the processor to perform any of the functions described herein. For example, a non-transitory, computer-readable storage medium storing a set of instructions capable of being executed by a processor to control the operation of a neurostimulator worn by a user, and that when executed by the processor, may cause the processor to: present the user with a set of waveform ensembles configured to modify the user's cognitive state; allow the user to select one waveform ensemble from the set of waveform ensembles; transmit the waveform ensemble parameters to the neurostimulator for application to the user's head by the neurostimulator; and allow the user to adjust the perceived intensity of the applied waveform ensemble during application of the waveform ensemble. The processor may be a processor of a hand-held device such as a smartphone (e.g., iPhone, Android-type phone, etc.), tablet computer (e.g., iPad), wearable computer (e.g., Google Glass, smartwatch, etc.), or the like.

For example, described herein are non-transitory, computer-readable storage mediums storing a set of instructions capable of being executed by a processor to control the operation of a neurostimulator worn by a user, and that when executed by the processor, causes the processor to: display, on a screen connected to the processor, a set of waveform ensembles configured to modify the user's cognitive state; allow the user to select one waveform ensemble from the displayed set of waveform ensembles; transmit the waveform ensemble from a wireless transmitter connected to the processor to the neurostimulator for application of the waveform ensemble to the user's head by the neurostimulator; and enable a control connected to the processor, wherein the user may adjust the control to modify the perceived intensity of the applied waveform ensemble during application of the waveform ensemble.

The set of instructions, when executed by the processor, may further cause the processor to allow the user to select a waveform ensemble from a sub-subset of waveform ensembles that are grouped by the cognitive state evoked by each of the waveform ensembles. The set of instructions, when executed by the processor, may further cause the processor to receive a signal from the neurostimulator indicating that an electrode has been attached to the neurostimulator.

For example, a set of instructions, when executed by the processor, may further cause the processor to receive a signal from the neurostimulator indicating that an electrode has been attached to the neurostimulator and to determine a type of the electrode from the signal from the neurostimulator. As discussed above, the set of instructions, when executed by the processor, may further cause the processor to allow the user to rate, tag, rank, or score the transmitted waveform ensemble and to store, transmit, or store and transmit the rating, tag, rank, or score.

For example, a user may provide a feedback score (numerical or otherwise) on efficacy, comfort, or both efficacy and comfort of the ensemble waveform, but may not necessarily rank this waveform vs. others. However, the user may also or alternatively rank the waveform compared to others (e.g., marking it as a favorite and/or providing a score, or as "thumbs up/thumbs down", etc.). A set of instructions, when executed by the processor, may also further cause the processor to allow the user to view and/or download a new waveform ensemble (e.g., from a remote server).

In some variations the set of instructions, when executed by the processor, further causes the processor to display a rating, tag, rank, or score of a waveform ensemble in the set of waveform ensembles.

As mentioned above, any of these apparatuses or devices may also be configured to allow the user to select and execute (during delivery of a waveform ensemble, or in some variations even when a waveform ensemble is not being delivered), a predetermined effect. For example, a set of instructions, when executed by the processor, may further allow the user to transmit an interrupt signal to the neurostimulator during the application of the waveform ensemble, wherein the interrupt signal temporarily modifies the application of the waveform ensemble for a predefined timer period. For example, the set of instructions, when executed by the processor, may further allow the user to transmit an interrupt signal to the neurostimulator during the application of the waveform ensemble, wherein the interrupt signal temporarily modifies the application of the waveform ensemble for a predefined timer period to evoke a phosphene. The set of instructions, when executed by the processor, may further allow the user to transmit an interrupt signal to the neurostimulator during the application of the waveform ensemble, wherein the interrupt signal is configured to transiently decrease and then increase (or transiently increase and then decrease) the perceived intensity of the waveform ensemble.

Any of these apparatuses may also be configured to help the user operate the device, including setting up and/or applying the electrodes. For example, a set of instructions, when executed by the processor, may cause the processor to show video including instructions for using the neurostimulator. The set of instructions, when executed by the processor, may cause the processor to display, in real-time, images from a camera connected to the processor so that the user may view an image of the user's head.

The set of instructions, when executed by the processor, may cause the processor to automatically estimate the number of electrodes the user has and prompt the user to purchase additional electrodes. The set of instructions, when executed by the processor, may cause the processor to track the application of the waveform ensemble by the user, including user adjustments to the perceived intensity. The set of instructions, when executed by the processor, may cause the processor to indicate past use information for each waveform ensemble in the set of waveform ensembles, including user adjustments to the perceived intensity of the waveform. The set of instructions, when executed by the processor, further causes the processor to indicate rating, tagging, ranking, or scoring information for individual waveform ensembles in the set of waveform ensembles based on ratings, tags, ranks, or scores made by other users. The set of instructions, when executed by the processor, may cause the processor to indicate rating, tagging, ranking, or scoring information for individual waveform ensembles in the set of waveform ensembles based on ranks made by the user.

Also described herein are methods and apparatuses that control the communication between a wearable neurostimulator and a user device that allows the user to exercise a high level of interaction and control of the delivery of the neurostimulation, including adjusting the perceived intensity as a waveform ensemble configured to evoke a cognitive state is being delivered, as well as allowing the user to select or choose, rank, and in some cases modify ensemble waveforms to be delivered. In variations in which the apparatus is a system including a wearable neurostimulator (with electrodes) and a user device (such as a handheld device with a processor, e.g., a smartphone configured to control the neurostimulator), the controlling device (user device) may first 'pair' with the neurostimulator, and establish secure wireless communication between the user device and the neurostimulator. This communication may be radio-frequency (e.g., Bluetooth, Zigbee, UWB, etc.) or other (optical, ultrasound, etc.). Once communication is established, it may be confirmed in an ongoing manner. If confirmation between the user device and the neurostimulator is lost or degrades below a threshold, the neurostimulator may enter a standby mode or a shutdown mode, which may prevent further stimulation and may be performed in a manner that optimizes safety without unduly interrupting neurostimulation. For example, if the neurostimulator unit loses communication with a previously paired user device, it may gradually turn down stimulation until stimulation ceases. A notification on the user device (e.g. a push notification within the app) may alert the user to the end of stimulation and unpairing of the device. This automatic shutdown behavior after connectivity with the user device is lost represents an important safety feature to ensure that the neurostimulator maintains a state of being controllable by the user device, including controls to stop, pause, or reduce the intensity of stimulation. In some variations the control device (e.g., the user device) may provide regular (e.g., every 400 ms or faster) bursts of instructions to the neurostimulator which may include parameters of or references to a waveform ensemble and user adjustments to the perceived intensity of the neurostimulation. Thus, it may be especially important to verify that the communication is both robust and correct, to avoid inappropriate adjustment of the intensity and/or incorrect or inappropriate waveforms being applied. For this reason, in some variations the user device and the neurostimulator may exchange multiple periodic (and in some variations scheduled) two-way or one-way confirmation signals, which may be duplex or half-duplex. Some or all communications may be encrypted, including salting and hashing. In particular, control communications (e.g., waveform ensemble information and/or adjustments to applied waveforms) may be encoded, including error correction coded, and the like.

For example, described herein are methods of controlling a neurostimulator with a user device in order to modify a user's cognitive state, the method comprising: wirelessly and periodically transmitting waveform ensemble parameters from the user device to a neurostimulator at a first time interval, during a stimulation period; wirelessly receiving in the user device a confirmation signal from the neurostimulator at a second time interval that is less than the first time interval; and stopping transmission of the waveform ensemble parameters if the confirmation signal is not received by the user device.

In some variations, the neurostimulator may stop (or ramp down) electrical stimulation if communication with the user device is lost or degrades below a threshold quality level. In general, the neurostimulator may be in constant (though in discrete intervals) communication and controllable by the user device, which may allow the user device to provide real-time or near real-time (within a few seconds) control of the neurostimulator.

Any of the methods described herein may also provide a method of controlling a neurostimulator with a user device in order to modify a user's cognitive state that includes: receiving in a user device, a signal from a neurostimulator indicating that an electrode has been attached to the neurostimulator; wirelessly and periodically transmitting waveform ensemble parameters from the user device to a neurostimulator at a first time interval during a stimulation period; wirelessly receiving in the user device a confirmation signal from the neurostimulator at a second time interval that is less than the first time interval; and stopping transmission of the waveform ensemble parameters if the confirmation signal is not received by the user device.

For example, any of these methods (or an apparatus configured to perform them) may determine a type of the electrode from the signal from the neurostimulator (e.g., energy, calm, lot number, etc.). Any of these methods may also include applying neurostimulation to the user from the neurostimulator using the received ensemble parameters from the user device, and/or receiving, in the user device, a signal from the neurostimulator indicating a contact between the user and an electrode of the neurostimulator.

In some variations, these methods may include receiving, in the user device, a signal from the neurostimulator indicating a contact between the user and an electrode of the neurostimulator, wherein the signal indicating the contact is encoded in the confirmation signal from the neurostimulator.

The methods may also include receiving, in the user device, a signal from the neurostimulator indicating (or correlated with) an impedance between the user and an electrode (or set of electrodes) of the neurostimulator, wherein the signal indicating the impedance is received about every minute (or, in some variations, less frequently, or more frequently). In some variations the method may include stopping or suspending stimulation by the neurostimulator if the impedance (or correlated value) is above a pre-defined threshold value.

In general, wirelessly and periodically transmitting ensemble parameters from the user device to a neurostimulator at a first time interval, during a stimulation period may include transmitting partial waveform ensemble parameters at an interval between some period of time (e.g., 10 msec to 10 seconds, 100 msec to 5 sec, 200 msec to 1 sec, 300 msec and 500 msec, about 400 msec, etc.). For example, wirelessly and periodically transmitting waveform ensemble parameters from the user device to a neurostimulator at a first time interval, during a stimulation period may include transmitting partial waveform ensemble parameters at about a 400 msec interval.

Wirelessly receiving in the user device a confirmation signal from the neurostimulator at a second time interval that is less than the first time interval may comprise wirelessly receiving in the user device the confirmation signal about every 300 msec, 250 msec, 200 msec, 150 msec, 100 msec, 50 msec, etc.

The methods described herein may also include pairing the user device to the neurostimulator before transmitting waveform ensemble parameters from the user device.

As mentioned above, in any of these variations, the transmission between the user device and the neurostimulator may be encrypted. For example, encryption may comprise encrypting the waveform ensemble parameters before transmitting them from the user device to the neurostimulator (or vice versa; encrypting information transmitted from the neurostimulator to the user device).

In general, also described herein are particularly effective methods of communicating information about the choices of neurostimulation protocols (ensemble waveforms also referred to as waveform ensembles), and methods of displaying a selected neurostimulation protocol in a manner that allows the user to easily see the perceived intensity and how it may be adjusted for comfort and/or efficacy. Also described herein are apparatuses (including software and user interfaces) configured to perform any of these methods.

For example, described herein are methods of modifying a subject's cognitive state using a neurostimulator worn on the subject's head, the method comprising: displaying a representation of a maximum perceived intensity of a waveform ensemble to be delivered by the neurostimulator on a wearable and/or hand-held user device; allowing the user to adjust the applied perceived intensity of the waveform ensemble being applied by the neurostimulator from the user device as the waveform ensemble is applied to the user; and displaying on the representation of the maximum perceived intensity of the waveform ensemble, a representation of the adjusted applied perceived intensity.

Displaying a representation of a maximum perceived intensity of a waveform ensemble to be delivered by the neurostimulator may include displaying a representation of the maximum perceived intensity of the entire waveform ensemble to be delivered by the neurostimulator. For example, the displayed entire ensemble waveform may be displayed as a pattern that represents the likely experienced intensity over the entire duration it is being (or will be) applied. The display may be graphical or interpretive. The display may be based, for example, on a perceived intensity (or maximum/peak perceived intensity). For example, the display may be based on a time-axis (linear or radial) display of a value for perceived intensity (e.g. perceived instantaneous intensity) calculated from the ensemble waveform (e.g., based off of the peak current, frequency, percent current imbalance, and duty cycle). For example, the perceived intensity (or maximum perceived intensity) may be calculated as the current×(11000/Frequency)×(0.5+the percent of current imbalance/200)×(percent duty cycle/100).

For example, displaying may include displaying the representation of the maximum perceived intensity as a linear display, in which representations of maximum perceived intensity for the waveform ensemble are arranged in a line. Alternatively, displaying may comprise displaying a representation of the maximum perceived intensity of the entire waveform ensemble as a loop, in which the representation of the maximum perceived intensity of a start of the waveform ensemble is displayed adjacent to the representation of the maximum perceived intensity of an end of the waveform ensemble.

In any of these variations the user may adjust the perceived intensity on the fly (e.g., during application). For example, the step of allowing the user to adjust the applied perceived intensity of the waveform ensemble may include presenting a control on the display of the user device to adjust the applied perceived intensity. Allowing the user to adjust the applied perceived intensity of the waveform ensemble may comprise adjusting the intensity of the waveform down at a first rate when the user adjusts the applied perceived intensity downward and adjusting the intensity of the waveform up at a second rate when the user adjusts the applied perceived intensity upward, wherein the first rate is faster than the second rate. For example, in some variations, there may be a limit on how far intensity can be increased in a fixed period of time (i.e., no more than 1 mA in 10 seconds, 1 mA in 20 seconds, 1 mA in 5 seconds, 1 mA in 1 second etc.). In some variations, there is a lockout for some period of time after increasing by that maximum amount, or a limiter for limiting the increase to this amount per unit time. User adjustments decreasing intensity may be made more quickly, however there may still be limits, preventing immediately decreasing the current and/or other waveform parameters affecting perceived intensity (e.g., frequency, duty cycle, and percent charge imbalance), because it may be uncomfortable to turn the perceived intensity of stimulation down too far and/or too fast. However, there is generally no lockout for turning the perceived intensity of stimulation down, and the maximum rate for turning it down is typically faster than the maximum rate for turning it up.

For example, described herein are methods of modifying a subject's cognitive state using a neurostimulator worn on the subject's head, the method comprising: displaying, for a plurality of time intervals, a representation of an instantaneous peak perceived intensity of a waveform ensemble to be delivered by the neurostimulator on a hand-held user device; allowing the user to adjust, from the user device, the applied perceived intensity of the waveform ensemble being applied by the neurostimulator, as the waveform ensemble is applied to the user, by selecting or adjusting a percentage of the peak perceived intensity from a control on the user device; and displaying on the representation of the instantaneous peak perceived intensity of the waveform ensemble, a representation of the adjusted perceived intensity for each time interval as the waveform ensemble is applied.

As discussed above, displaying may include displaying a representation of the instantaneous peak perceived intensity of the entire waveform ensemble to be delivered by the neurostimulator. For example, displaying may include displaying the representation of the instantaneous peak perceived intensity as a linear display, in which representations of instantaneous peak perceived intensity for the waveform ensemble is arranged in a line. In some variations, displaying comprises displaying a representation of the instantaneous peak perceived intensity of the entire waveform ensemble as a loop, in which the representation of the instantaneous peak perceived intensity of a start of the waveform ensemble is displayed adjacent to the representation of the instantaneous peak perceived intensity of an end of the waveform ensemble.

As mentioned above, allowing the user to adjust the applied perceived intensity of the waveform ensemble may include presenting a slider or dial on the display of the user device to adjust the applied perceived intensity. In some variations the user may adjust the perceived intensity using a pair of buttons (one to increase, one to decrease). In any of the variations described herein, the user device and/or neurostimulator may be configured so that there is a default or initial value of the user adjustment to the perceived intensity of the waveform ensemble. The default or initial value may be the same for all users (i.e. 50% of the values of the perceived intensity from the waveform ensemble) or the default or initial value may be customized for a user based on adjustments made during delivery of an ensemble waveform previously that are tracked and stored by the system with an association to that user (e.g. user ID associated with the tracked and stored data). The default or initial value may be customized for a user based on demographic, psychographic, and/or physiologic data. During an ensemble waveform stimulation, a user adjustment may be an adjustment to the current, frequency, current and frequency, or any combination of: current, frequency, duty cycle, percent charge imbalance (which may also be referred to as percent DC), and the presence and waveform shape of amplitude modulation.

For example, allowing the user to adjust the applied perceived intensity of the waveform ensemble may comprise adjusting the intensity of the waveform down at a first rate when the user adjusts the applied perceived intensity downward and adjusting the intensity of the waveform up at a second rate when the user adjusts the applied perceived intensity upward, wherein the first rate is faster than the second rate.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A and 1D illustrate the approximate regions for a first placement configuration of the electrodes for inducing a cognitive state of attention, alertness, or mental focus.

FIG. 1B schematically illustrates the approximate regions for a second placement configuration of the electrodes for enhanced attention, alertness, or mental focus.

FIGS. 1C and 1E illustrate the approximate regions for another placement configuration of the electrodes for enhancing a calm or relaxed mental state FIGS. 2A and 2B schematically illustrates a TES waveform according to one embodiment of the invention.

FIGS. 3B-3G illustrate another example of a neurostimulator as described herein.

FIGS. 3H-3K illustrate a first example of one variation of an electrode assembly, configured as a "calm" electrode assembly.

FIGS. 3L-3o illustrate a second example of one variation of an electrode assembly, configured as an "energy" electrode assembly.

FIG. 12 illustrates a flow chart for user control of a neurostimulator by controlling a waveform ensemble in accordance with some embodiments of the invention.

DETAILED DESCRIPTION

Figure 2A:
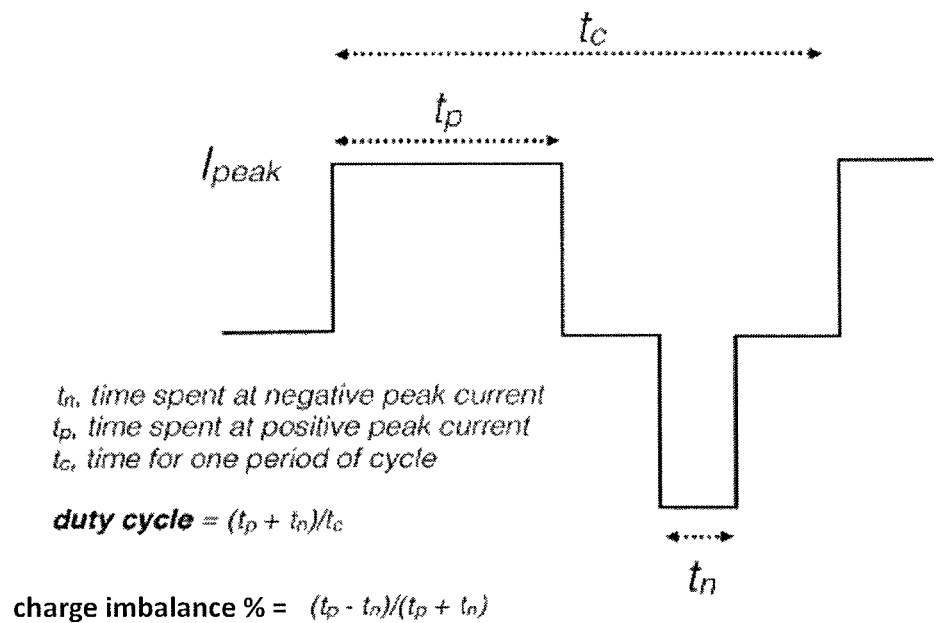

The following description of the various embodiments of the invention is not intended to limit the invention to these embodiments, but rather to enable any person skilled in the art to make and use this invention.

Described herein are methods and apparatuses (including devices and systems) for user control of neurostimulation waveforms, particularly, transdermal electrical stimulation (TES) waveforms. In general, the methods, apparatuses, and systems may allow a user to control neuromodulation with electrical stimulation to induce a beneficial or desired change in cognitive function and/or cognitive state. In general, a user may wear a neuromodulation device and apply one or more waveforms using the neuromodulation device to induce a cognitive effect. In general, the user may control the wearable neuromodulation device through a user device. A user device may be used to control the applied waveforms ("ensemble waveforms") for use in a transdermal electrical stimulation protocol. A system may include the wearable neuromodulation device, and the user computing device for control of the transdermal electrical stimulation (TES) waveforms.

System Description

In general, a neurostimulation system as described herein may include a lightweight, wearable neurostimulator device (neurostimulator) that is configured to be worn on the head and a consumable/disposable electrode assembly; in addition a device that may be worn and/or held by the user ("user device") which includes a processor and wireless communication module may be used to control the application of neurostimulation by the wearable neurostimulator. Although the configuration and operation of the user device is of particular interest herein, this disclosure may also benefit from a brief description of possible features and aspects of the overall system, including the neurostimulator and/or the electrode assemblies used therewith.

The user device may also be referred to herein as a controller, and the controller (user device or user computing device) is typically separate from but communicates with the neurostimulator. For example, in some variations the controller may be a user device that wirelessly communicates with the neurostimulator. In some variations the controller is a mobile telecommunications device (e.g., smartphone or tablet) or wearable electronics (e.g., Google glass, smart watch, etc.), being controlled by an application that sends instructions and exchanges 2-way communication signals with the neurostimulator. Any of these embodiments may be referred to as handheld devices, as they may be held in a user's hand or worn on the user's person. However, non-handheld control user devices (e.g., desktop computers, etc.) may be used as well. The user device may be a general purpose device (e.g., smartphone) running application software that specifically configures it for use as a controller, or it may be a custom device that is configured specifically (and potentially exclusively) for use with the neurostimulators described herein. For example, the controller may be software, hardware, or firmware, and may include an application that can be downloaded by the user to run on a wireless-connectable (i.e. by Bluetooth) device (e.g., handheld device such as a smartphone or tablet) to allow the user to select the waveforms delivered by the neurostimulator, including allowing real-time modulation of the delivered neurostimulation to modify the user's cognitive-state as described herein.

For example the system can be operated to induce either "calm" states of mind or "energetic" states of mind. Operating the system to induce a state of increased energy can be alternatively described as one or more of: enhancing focus and attention; enhancing alertness; increasing focus and/or attention; enhancing wakefulness; increasing subjective feeling of energy; increasing objective physiological energy levels; increasing motivation; increasing physiological arousal; and evoking a physical sensation of warmth in the subject's chest. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; improved quality of sleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis; a reduction in biomarkers of stress, anxiety, and mental dysfunction; anxiolysis; a state of mental clarity; enhanced physical performance; resilience to stress; a physical sensation of relaxation in the periphery; and a perception of feeling the heartbeat.

For example, to enhance energy, the electrode apparatus may be attached to the user's temple and behind the user's ear (e.g., mastoid region). To induce a state of increased calm, the electrodes may be attached to the user's temple and the back of the user's neck. In both examples, the neurostimulator may apply an ensemble waveform for about 2-30 min (e.g., 3-30 min, 4-30 min, 5-30 min, 2-35 min, 2-40 min, 2-45 min, 2-50 min, 2-55 min, 2-60 min, or longer) that is made up of different "blocks" having repeated waveform characteristics; the waveform ensemble may include transition regions between the different blocks. In general, at least some of the waveform blocks (and in some variations most or all of them) generally have a current amplitude of >5 mA (e.g., between 5 mA and 40 mA, between 5 mA and 30 mA, between 5 mA and 22 mA, etc.), and a frequency of >750 Hz (e.g., between 750 Hz and 25 kHz, between 750 Hz and 20 kHz, between 750 Hz and 15 kHz, etc.), the current is typically biphasic and is typically charge imbalanced, and has a duty cycle of between 10-99% (e.g., between 20-95%, between 30-80%, between 30-60%, etc.). One or more of these characteristics may be changed during stimulation over timescales of every few seconds to minutes. In some cases, parameters may change quickly (i.e. on a timescale of 100s of milliseconds). Moreover, ramping may be included in the transitions between any parameter values, so that the component of the waveform ensemble is continuously changing.

Figure 3A:
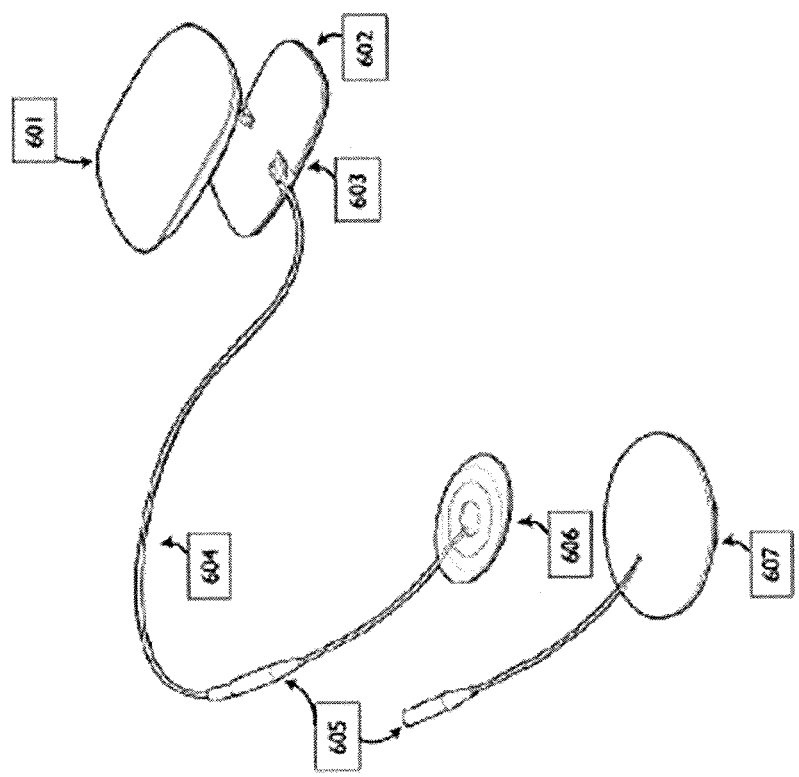
FIG. 3A illustrates one example of a neurostimulator according to one embodiment of the invention.
Figure 3Q:
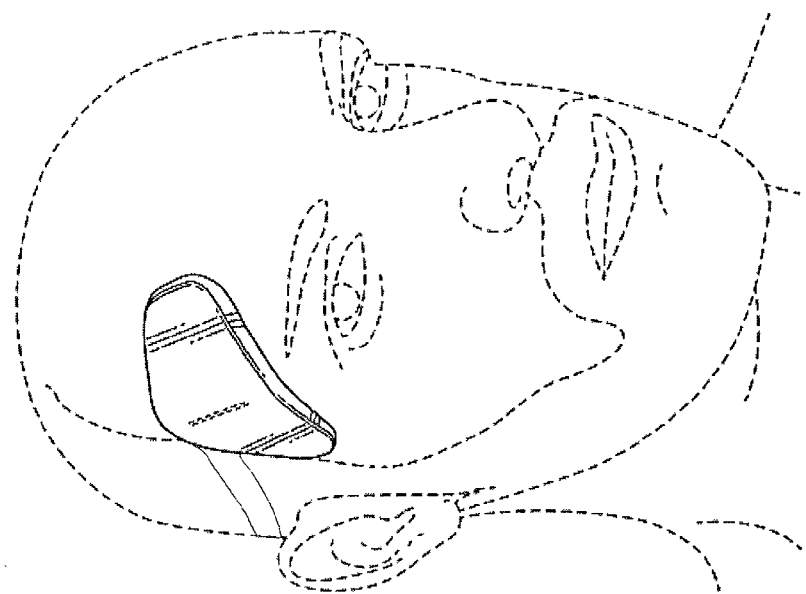
FIG. 3Q illustrates the neurostimulator device worn on the subject's head.

When worn, the system may resemble the system shown in FIG. 3Q, having an electrode assembly attached at two locations (points or regions) on the subject's head and/or neck and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g. enclosing the circuitry, power supply, and wireless communication components such as a rechargeable battery and charging circuit, Bluetooth chip and antenna, microcontroller, current source configured to deliver waveforms with a duration of between 10 seconds and tens of minutes. A neurostimulator may also include safety circuitry. The neurostimulator may also include circuits to determine that the electrode is attached and what "kind" of electrode it is (i.e., for the calm or the energy mode; or indicating the batch and/or source of manufacture). FIGS. 3A and 3B-3G illustrate two variations of a neurostimulator.

For example, FIG. 3A illustrates a first example of a neurostimulator as described herein. In FIG. 3A, the neurostimulator is shown with a pair of electrodes attached. A first electrode 601 is coupled directly to the body 603 of the TES applicator 602, and a second electrode 606 is connected by a cable or wire 604 to the body 603 of the applicator 602. These electrodes are separate from each other, and may be replaceable/disposable. Different shaped electrodes 607 may be used with the same re-usable neurostimulator. The neurostimulator in this example includes a rigid outer body, to which the pair of electrodes is attachable, making electrical contact via one or more plug-type connectors.

FIGS. 3B-3G illustrate another, preferred embodiment of a neurostimulator as described herein. In this variation the neurostimulator is also a lightweight, wearable neurostimulator that attaches to an electrode, and includes contacts for making an electrical connection with two (or potentially more) electrically active regions (e.g., anodic and cathodic regions) on the electrode(s). However, in this example, the neurostimulator is configured to operate with a cantilevered electrode apparatus, and to attach both mechanically and electrically to the electrode apparatus at a region that is off-center on the bottom (underside or skin-facing side) of the neurostimulator, allowing one end region to be held securely to the skin while the other edge region is not pinned in this way. The "floating" end may therefore adjust slightly to different curvatures of the head, even while the electrode assembly (which may be flexible) is securely held to the skin. Thus, this cantilevered attachment mechanism may enhance comfort and adjustability of the device. In addition, the neurostimulator device may be configured specifically so that it can be comfortably worn at the user's temple, even in users wearing glasses. For example, the apparatus may be configured so that the skin-facing side (which connects to the electrode assembly via one or more connectors) is curved with a slightly concave surface having a slight twist angle. This curve shape may help the apparatus fit more snugly (better) to the surface of the temple. In addition, one end of the device (the end to be positioned in-line with the edge of the user's eye and the user's ear) may be thinner (e.g., less than 2 cm, less than 1.5 cm, less than 1 cm, less than 0.8 cm, etc.) than the opposite end, which may be worn higher up on the temple.

For example, FIGS. 3B-3G illustrate front, back, left side, right side, top and bottom perspective views, respectively of a variation of a neurostimulation device (neurostimulator or electrical stimulator) that may be used with a cantilever electrode apparatuses. The overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner) may fit between the eyebrow and hairline, while the wider portion is positioned up in the forehead area where there is less likely to be hair.

In FIGS. 3B-3G the various edges of the neurostimulator are labeled, based on where the apparatus will be worn by the subject, as is illustrated in FIG. 3Q. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes having rounded/smooth transitions between the three sides, as illustrated. The subject-facing surface is specifically contoured to fit in the predefined orientation, making it difficult or impossible for a subject to misapply and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

Within the housing, any of the neurostimulators described herein may include a processor (e.g., microprocessor) or controller, a wireless communication module that is connected to the processors, and a power source (e.g., battery, etc.). The power source may be configured to provide power to the internal circuitry and/or the circuitry driving current between anodic and cathodic regions of the electrodes when worn by the user. The power supply may be high-voltage power supply, e.g., able to provide up to 60 V across these electrode terminals. In general, the apparatus may also include circuitry that is configured to regulate the energy (e.g., current) delivered as required by the processor, which may in turn receive instructions via the wireless communications module from a controller. The controller may also communicate information, and in particular information about the electrodes, including confirming that the electrode assembly is connected and/or what type (e.g., calm, energy, make/model/size, batch, etc.) of electrode assembly is attached, and an indicator of the contact with the user's skin (e.g., impedance, proportional to impedance, or a value from which an estimate of the impedance of the electrode(s) may be derived).

As will be described in greater detail herein, the electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g. at the temple and the back of the neck and/or behind the ear). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on the region over the mastoid bone, behind the subject's ear (energy electrode configuration) or a region across the user's neck at the base of the hairline, e.g., near the midline of the neck (calm electrode configuration).

The electrode apparatus may be printed (e.g., by flexographic printing, laser printing with conductive ink, silkscreening, etc.) on a flexible plastic substrate (flex substrate) and may also include a pair of connectors (snaps) on the side opposite the skin-facing electrodes. The electrode active regions on the back of the assembly may include a layer of conductor (e.g., silver), over which a layer of Ag/AgCl is deposited that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

As mentioned above, there may be multiple configurations (e.g., shapes) of the electrode assembly, and, as described in greater detail herein, the electrode assembly may generally be formed on a flexible material ('flex circuit' material) and mechanically and electrically connected to the neurostimulator.

FIGS. 3H-3K illustrate one variation of a cantilever electrode apparatus ("electrode apparatus") that may be used with a neurostimulator and may be worn on a subject's head. This variation may be referred to as a "calm" configuration, as it is adapted to connect to a user's temple region and the back of a user's neck. In this example, the cantilever electrode apparatus 100 includes a plurality of electrode portions (two are shown) 103, 105. In FIG. 3H, a front perspective view is shown. The front side is the side that will face away from the subject when worn. The cantilever electrode apparatus is thin, so that the electrode portions include a front side (visible in FIGS. 3H and 3I) and a back side (visible in FIG. 3K). As shown in the side view of FIG. 3J, the device has a thin body that includes the electrode portions 103, 105 as well as an elongate body region 107 extending between the two electrode portions. The elongate body is also thin (having a much larger diameter and height than thickness). The thickness is shown in FIG. 3J.

In this example, two connectors 115, 117 (electrical and mechanical connectors, shown in this example as snaps) extend from the front of the cantilever electrode apparatus. The front of the first electrical portion 103 may also include an optional foam and/or adhesive material 121 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 3H-3K as about 0.72 inches). The second electrode portion may also include a foam or backing portion 123. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 3K shows a back view of this first example of a cantilever electrode apparatus. In this example, the first 103 and second 105 electrode portions are also shown and include active regions 133, 135. The active regions are bordered by adhesive 140. The first 103 electrode portion includes, on the back (patient-contacting) side, a first active region 133, portion of which is bounded, e.g., around its entire circumference, or at least on a portion of the circumference, by an adhesive 140. The active region may include a conductive material (e.g., electrically conductive gel). Similarly, the back of the second electrode portion 105 includes the second active region 135 which is surrounded on two sides by an adhesive material 140 to the edge of the electrode. The adhesive may be any biocompatible adhesive that can releasably hold the material to the skin.

FIGS. 3L-3o illustrate another example of a cantilever electrode apparatus. This example is very similar to the variation shown in FIGS. 3H-3K, but may be referred to as an "energy" configuration as it is configured to contact both the user's temple region and a region behind the user's ear, over the mastoid region. The connectors (snaps 417, 415) are in the same position as shown in FIGS. 3H-3K, as are the shape of the first electrode portion 403 and foam/backing material 421 (which may also or alternatively be an adhesive material). An advantage of having multiple electrode apparatuses with the same shape is that they can be used interchangeably with a single neurostimulator device. However, the example shown in FIGS. 3L-3o includes a different overall shape, and may be used to connect, for example, to different regions of the patient's head/neck. In particular, the portion of the substrate forming the elongate body region 407 extending between the two electrode portions 403, 405 is shaped slightly differently. In this example, the cantilever electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 433 of the first electrode portion 405 in electrical contact with the skin at the temple region and using the adhesive material 440 surrounding the electrically active region 433 to hold the electrically active region (and the attached neurostimulator) securely in position on the subject's skin, the second electrically active region may also be adhesively 441 held to skin so that the second electrically active region 435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 3H-3K and 3L-3o. The bend or curve, in which the elongate body may even double back on itself, may allow the material to flex or bend to allow it to be adjustably positioned over and/or around the subject's head, as shown in FIGS. 3P and 3Q, for example.

Figure 3P:
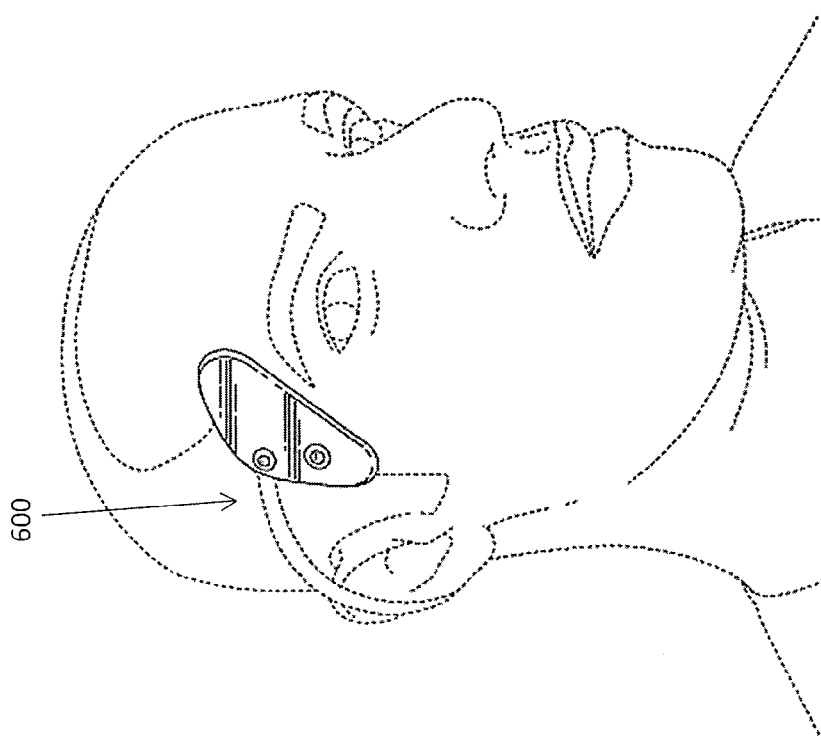
FIG. 3P illustrates the application of an electrode assembly that may be worn on the subject's head, and/or head and neck to induce a cognitive effect.

FIG. 3P illustrates a cantilever electrode apparatus (similar to those shown in FIGS. 1A and 4A) worn on a subject's head. As illustrated, the apparatus is positioned with the first electrode portion adhesively attached at the temple region and a second electrode portion attached to a region behind the head (e.g., behind the ear or neck region, not shown). A neurostimulator (not shown in FIG. 3P) may be attached to the cantilever electrode apparatus either before or after it is applied to the subject. In the example shown in FIG. 3P, the electrode apparatus is an energy configuration and is shown attached (worn) on the subject's temple region and on the region behind the ear (not shown). As shown in FIG. 3Q, the neurostimulator may be attached to the front side of the cantilever electrode apparatus by snapping onto the proud connectors, while the elongate body region 107 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in U.S. patent application Ser. No. 14/320,443, titled "TRANSDERMAL ELECTRICAL STIMULATION METHODS FOR MODIFYING OR INDUCING COGNITIVE STATE," filed on Jun. 30, 2014, Publication No. US-2015-0005840-A1 and herein incorporated by reference in its entirety.

In use, a user may interact with a controller (e.g., a smartphone controlled by application software/firmware) that pairs with the neurostimulator (e.g. by Bluetooth). The user may operate the controller to select the operational mode, e.g., the type of cognitive effect to be induced, such as an energy mode or calm mode, and/or the device could automatically detect a mode based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e. current amplitude, frequency, duty cycle, charge imbalance, shorting/capacitive discharge, amplitude modulation, etc., and these parameters may change at pre-specified times as they change to new segments; a transition period may be included to switch between block properties. Once the user selects an ensemble waveform, they can start the neurostimulation and the user can control or change the perceived intensity (e.g., by changing the perceived intensity up or down by a user interface element of an app), pause, or stop the session using the controller (i.e. app running on a smartphone). In general, the perceived intensity can be scaled by the user between 0-100% of a target perceived intensity (e.g., a target current, frequency, duty cycle, charge imbalance, amplitude modulation, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect or skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e. tweet your experience), feedback about a session, and analysis/history of previous use. In general, the system may also be configured to pass data to and from the controller and/or the neurostimulator and to/from a remote server via the Internet. These data may include user information, waveform data, information about the function or state of the hardware device or electrode assembly, etc.

In general, described herein are general TES waveform parameters that may be used to invoke, enhance, or modify a variety of cognitive states. Although the apparatuses and methods described herein may be used to provide TES to induce and/or modify a variety of cognitive states, two particular examples are described in detail herein, including inducing enhanced attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

Thus, a generic neurostimulator for modifying a cognitive state may include a pair of electrodes (or two sets of electrodes, e.g., one may be referred to as "anode" and one as "cathode" for convenience), that can be applied to specific regions of the subject's body and used to provide TES stimulation within the relatively high-intensity, high-frequency ranges described as effective herein. Current is typically applied between the anode and cathode electrodes (or groups of anodes and cathode electrodes). Without being bound by a particular theory of operation, the current may be passed through the body between the anode and cathode, potentially applying energy in an appropriate treatment regime to underlying neural tissue (cranial nerves, brain, etc.) in a particular neural pathway to result in the desired target effect (e.g., attention, alertness, or mental focus—or inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration. For example, a first placement configuration for inducing a cognitive state of attention, alertness, or mental focus, which may be referred to as "configuration A" or "configuration 2" may include a first electrode applied to the subject near the temple area (e.g., laterally to the eye, such as slightly above and to the right of the right eye or above and to the left of the left eye) and a second electrode positioned behind the ear on the same side as the first electrode in the mastoid region (e.g., on or near the mastoid). FIGS. 1A and 1D illustrate approximate regions for electrode placement of this configuration (configuration A, "energy"). In this variation, a first electrode 10, 302 is positioned at the temple, and a second electrode 11, 303 is positioned at the mastoid region, behind the ear of the subject 15, 300. High-intensity TES stimulation (as described in greater detail below) of this region may result in enhanced attention, alertness, or mental focus. FIG. 1B schematically illustrates another configuration for enhanced attention, alertness, or mental focus. The second configuration (referred to for convenience herein as "configuration C" or "configuration 1") may include placement of a first electrode 10 on the temple area (e.g., laterally to the eye, such as slightly above and to the right of the right eye or above and to the left of the left eye) and a second electrode 13 positioned on the forehead, (e.g., near or above the nasion).

Another configuration (referred to herein for convenience as "configuration B" or "configuration 3") may include an electrode 10 positioned on the subject's skin near the subject's temple area (e.g., laterally to the eye, such as slightly above and to the right of the right eye or above and to the left of the left eye and a second electrode 12, 306 on the subject's neck, e.g., centered on the midline and oriented horizontally along the base of the hairline and partially overlapping the spinal cord). FIGS. 1C and 1E illustrate the approximate regions for electrode placement of configuration B. TES stimulation of this region may result in enhancing a calm or relaxed mental state.

The electrode placements describe above in FIGS. 1A-1E may also be used for eliciting a phosphene, which is described in greater detail below. Phosphenes may be induced by noninvasive transdermal electrical stimulation using the apparatuses described herein. A first periorbital transdermal electrode (in close proximity to the eye) and a second transdermal electrode for which positioning is less important (i.e. the second electrode can be placed on the contralateral periorbital area, skull, neck, shoulder, leg, or other part of the body of a subject) deliver a transdermal current waveform to elicit a phosphene. In FIG. 1D, subject 300 has single mastoid electrode behind the ear 303 and periorbital electrode 302, which is the same general configuration as the "energy" configuration shown in FIG. 1A for evoking the energy response described herein. In FIG. 1E, subject 300 has single neck electrode 306 and two periorbital electrodes 304, 305 that can be isoelectric or separate circuits that can be triggered independently to induce distinct phosphenes with regard to retinal location; this configuration is the same general configuration as the "calm" configuration of FIG. 1C, and described herein.

In general, peak stimulation intensities above at least 3 mA may be advantageous for transdermal electrical stimulation that causes neuromodulation by targeting the brain, nerves (e.g., cranial nerves, vagal nerve, peripheral nerves), and/or spinal cord. To achieve these peak intensities without causing pain, irritation, or discomfort in a subject may require appropriate electrodes and TES waveforms. Beneficial electrodes may have pH buffering properties and may contain components for uniformly (or more uniformly) delivering current across the dermal-facing portion of the electrode.

The TES waveforms for use with any of the configurations described herein may be a pattern of currents delivered into tissue of a user (e.g. transdermally). Although there may be variations (optimizations) of these waveforms and electrical protocols for each configuration (electrode placement) and each target cognitive state, in general, the patterns may be within the same range of values to provide high-intensity, high frequency, high-duty cycle and not charge balanced (e.g., DC offset) signals that are applied to robustly evoke a response in most individuals while causing at most a low level (e.g. minimal or none) of discomfort and/or pain.

The TES waveforms may also be referred to herein as ensemble waveforms, because they typically include a plurality (e.g., 3 or more) of component waveforms having a predetermined value for each of: current amplitude ("intensity"), frequency, percent charge imbalance (also referred to herein as "DC offset"), duty cycle, amplitude modulation (in some variations), and in some variations capacitive discharge. These component waveforms each also have a duration, and are connected together in a sequence to evoke the desired cognitive effect. Some of these component waveforms forming the ensemble waveform are ramps, in which the waveform is a ramp up to the waveform component value (frequency, intensity, percent charge imbalance, and duty cycle) when a waveform component has changed from a previous value.

The time varying pattern of electrical stimulation delivered transdermally and/or transcranially to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g. amplitude modulation at one or more frequencies, including bust stimulation and sine-wave modulated stimulation), and more complex (including repeated, random, pseudo-random, and chaotic patterns). In operation, the device may provide current flow at target areas (e.g., in the brain, facial nerves, vagal nerve, and/or other neuronal targets) to induce neuromodulation when appropriate electrode configurations and stimulation protocols are delivered.

In general, a TES waveform may be defined by a duration, direction (and whether unipolar or biphasic), peak current, and frequency. FIG. 2A schematically illustrates a TES waveform according to one embodiment of the invention. In some embodiments, a TES waveform is further defined by a percent duty cycle, percent direct current (also referred to as percent charge imbalanced), ramping or other amplitude modulation, one or multiple frequency components, phase relationship of biphasic current, flat or structured noise, wave shapes (i.e. sawtooth, triangular, sine wave, square wave, exponential, or other wave shape), capacitance compensation features, or other parameters as discussed in U.S. patent application Ser. No. 14/091,121, titled "WEARABLE TRANSDERMAL ELECTRICAL STIMULATION DEVICES AND METHODS OF USING THEM", filed on Nov. 26, 2013, now U.S. Pat. No. 8,903,494, which is herein incorporated by reference in its entirety. As used herein, 'percent duty cycle' may refer to the proportion of a cycle of a waveform that causes non-zero (or nominally non-zero) current to be delivered transdermally (see equation, FIG. 2). Further, 'percent direct current' may refer to the non-zero portion of a waveform cycle that is positive-going (see equation, FIG. 2A).

Inducing significant, robust, and/or reliable cognitive effects typically requires an appropriate TES waveform defined by a set of parameters. A stimulation protocol ('TES waveform') may define the temporal pattern of current delivered to an anode-cathode set and can incorporate one or more waveform components including but not limited to: direct current, alternating current, pulsed current, linear current ramp, nonlinear current ramp, exponential current ramp, modulation of current, and more complex (including repeated, random, pseudo-random, and chaotic patterns). In operation, the device may provide current flow at target areas (e.g., in the brain, in cranial nerves) to induce neuromodulation when appropriate electrode configurations and stimulation protocols are delivered.

In order to elicit a phosphene, a large, rapid change in current between a periorbital electrode and another electrode may be used. The first time derivative of the current and the magnitude of change in current are both factors in reliably inducing phosphenes—for both, bigger is better for phosphene induction. For instance, a change in peak current of at least 5 mA over less than one second is a TES waveform feature effective for inducing a phosphene reliably. In addition, modulation of the amplitude of the applied waveforms ("amplitude modulation", or "burst mode") is another effective way to trigger phosphenes when the frequency of bursting (of the higher frequency carrier) or amplitude modulation is <100 Hz (particularly less than 70 Hz and optimally between about 8 Hz and about 50 Hz).

Figure 2B:
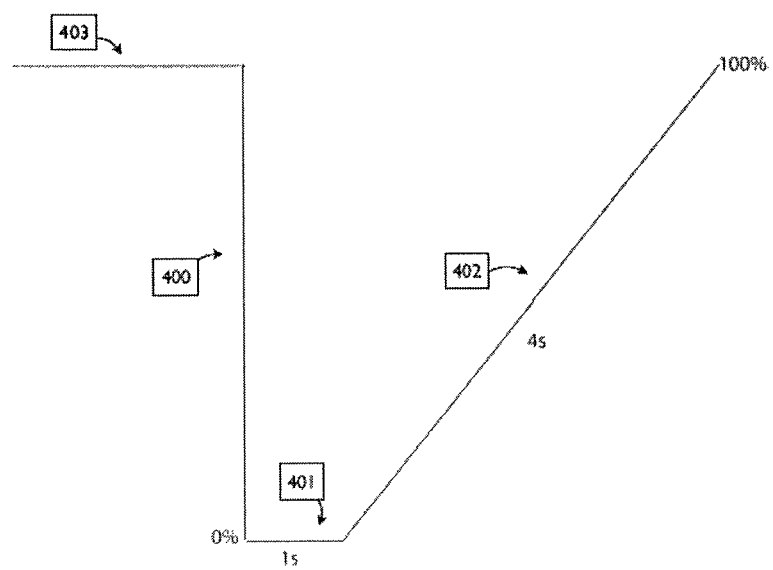

FIG. 2B shows the peak current (or voltage) value of a TES waveform that is an exemplar for inducing a phosphene. High peak current 403 (which can be positive or negative in different variations) is delivered to a subject for a period of time then is reduced rapidly 400, held at a low value for one second 401, then gradually ramped but up to the high intensity 402 that enables another phosphene to be induced at a later timepoint. In variations of the invention, a rapid, large transient increase in current intensity can also be effective for inducing a phosphene. As described herein, the peak current (or voltage) value can correspond to the peak of pulsed, alternating current, or another high frequency TES waveform. For most people, the most effective waveform for eliciting a phosphene is a reversal of polarity on the electrode above the eye from negative to positive (or in the case or charge-imbalanced biphasic waveforms—from mostly negative to mostly positive).

A set of waveform parameters may be selected based on the desired cognitive effect and the number of electrodes, positions of electrodes, sizes of electrode, shapes of electrode, composition of electrodes, and anode-cathode pairing of electrodes (i.e., whether a set of electrodes is electrically coupled as an anode or cathode; also whether multiple independent channels of stimulation are present via current sources driving independent anode-cathode sets). Changing any of the features in the preceding list may require adapting a TES waveform by changing one or more parameters in order to achieve a desired cognitive effect. For example, for high frequency biphasic stimulation, current intensity can be ramped up very quickly without discomfort relative to direct current stimulation. This feature is advantageous for being able to induce beneficial cognitive effects quickly without painful, irritating, or distracting side effects.

As mentioned above, a waveform ensemble is a composition of waveforms that are configured to evoke a specific neural response or a specific cognitive effect. Some waveforms (waveform ensembles) are configured to induce a calm state of mind and may be used with the specific electrode configuration such as illustrated in FIGS. 1C and 1E. Some waveforms are configured to induce a state of mind that is more energetic and focused, and these waveforms may be used with the electrode configurations as illustrated in FIGS. 1A and 1B, and 1D. Waveform ensembles may also include "nested" waveforms, which may comprise shorter waveform elements across at least two timescales to achieve extended cognitive effects. Waveform ensembles including nested waveforms may be used to induce cognitive effects that are sustained, more intense, or that provide a related but subjectively distinct experience (e.g., a first TES stimulation waveform may cause increased motivation while a second, related TES stimulation waveform induces an increase in mental clarity and focus). An apparatus (including the applicator and/or remote processor paired with the applicator) may include these various waveform sets and may be selected (and in some cases modified) by the subject.

As mentioned above, a neurostimulator adapted for use with the methods and apparatuses described herein may include hardware and software systems for TES such as: a battery or power supply safely isolated from mains power; control hardware, firmware, and/or software for triggering a TES event and controlling the waveform, duration, intensity, and other parameters of stimulation of each electrode; and one or more pairs of electrodes with gel, saline, or another material for electrical coupling to the scalp. The hardware, firmware, and software for TES may include additional or fewer components. Hardware, firmware, and software for TES may include a variety of components.

TES methods and the various configurations described herein may be used with any TES system capable of delivering an appropriate TES waveform transdermally. In general, a TES system may use adherent electrodes and/or electrodes held in place by a wearable apparatus (i.e. cap, headband, necklace, eyeglass frame, or other form factor that enables an electrode to be in physical contact with the subject's skin). In general, the power supply, current controller, and other electronic circuitry (e.g. safety circuitry and, optionally, wireless communication chip sets) of a TES controller may be in a handheld, tabletop, or other portable controller system; wearable components that connect directly to one or both electrodes or connect to the electrodes by wire and are otherwise wearable by a user (or placed within another worn structure (e.g. a headband or armband; a pocket; a necklace, earring, or eyeglass frame)); or completely disposable and integrated with one or more transdermal electrodes of the system.

For example, embodiments of the invention include methods for using electrodes according to configuration A and/or configuration B to induce a cognitive effect as described above by delivering an appropriate TES waveform from a transdermal electrical stimulation system to a subject. Generally, embodiments of the invention also include systems whereby a TES apparatus includes a power supply (e.g. battery), current control and safety circuitry, processor (i.e. microprocessor, microcontroller or the like), electrically conductive connectors and/or cables connecting to the anode(s) and cathode(s), and, optionally, a wireless communication module, in addition to a non-transitory computer-readable storage medium storing a set of instructions capable of being executed by the processor that, when executed by the processor causes a TES waveform to be delivered transdermally between the anode (or set of isoelectric anodes) and cathode (or set of isoelectric cathodes).

Figure 4:
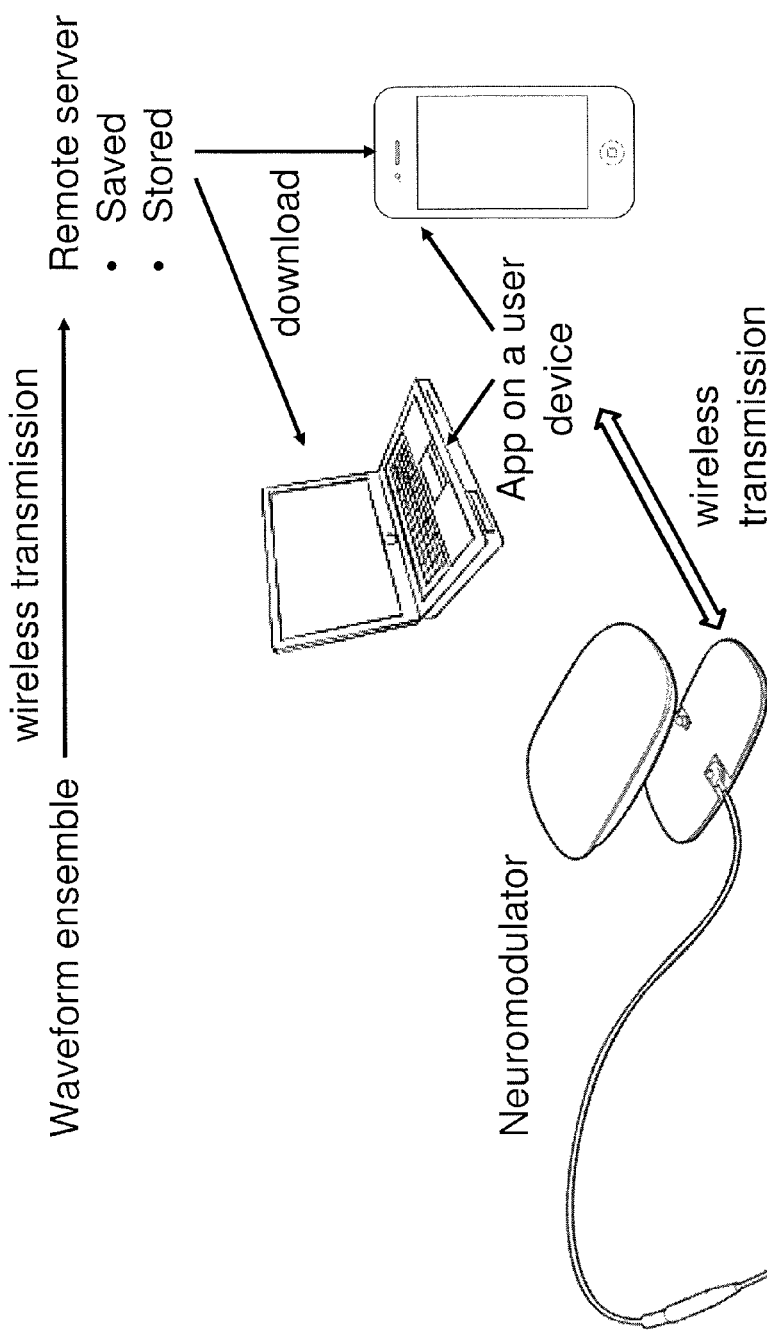
FIG. 4 schematically illustrates a system for user control of neurostimulation in accordance with various embodiments of the present invention.

FIG. 4 schematically illustrates a system for user control of neurostimulation in accordance with various embodiments of the present invention. In some embodiments, the system may include a neuromodulator and an application on a user computing device. The user computing device may be selected from the list including but not limited to: a smartphone running an Android or iOS operating system such as an iPhone or Samsung Galaxy, a tablet such as an iPad, a personal computer including laptops and desktop computers, a wearable computing device (e.g. Google Glass or a smartwatch), a remote controller, or any other suitable computing device. The user computing device may further include a physiological sensor (or be paired with a physiological sensor to receive data from that sensor) (e.g. sensor of heart beats, breathing, gaze direction, pupil dilation, brain activity (i.e. by EEG), circulating molecules, etc.). In some embodiments, the neuromodulator may include at least one pair of transdermal electrodes and a controller of the neuromodulator. In some embodiments, the adherent or wearable neurostimulator may comprise components: battery, memory, microprocessor, current control circuitry, fuse and other safety circuitry, wireless antenna and chipset, and waveform generator. The user computing device may include components: wireless antenna and chipset, graphical user interface, one or more display elements to provide feedback about a TES session, one or more user control elements, memory, and microprocessor. The application may be downloaded by the user to the user computing device to run and control the neurostimulator for the TES neurostimulation sessions. In some embodiments, the user computing device may be a remote controller configured to control the neurostimulator; the application may be stored on the remote controller. One of ordinary skill in the art would appreciate that a neurostimulator may comprise a variety of components, the user computing devices may include a variety of computing devices, and the application may be saved on a remote server, a data storage device, and/or the user computing devices.

The neurostimulator may be configured to communicate bidirectionally with a wireless communication protocol to the user computing device. The system can be configured to communicate various forms of data wirelessly, including, but not limited to, trigger signals, control signals, safety alert signals, stimulation timing, stimulation duration, stimulation intensity, other aspects of a stimulation protocol, electrode quality, electrode impedance, and battery levels. Communication may be made with devices and controllers using methods known in the art, including but not limited to, RF, WIFI, WiMax, Bluetooth, BLE, UHF, NHF, GSM, CDMA, LAN, WAN, or another wireless protocol. Pulsed infrared light as transmitted for instance by a remote control is an additional wireless form of communication. Near Field Communication (NFC) is another useful technique for communicating with a neuromodulation system or neuromodulation puck. One of ordinary skill in the art would appreciate that there are numerous wireless communication protocols that could be utilized with embodiments of the present invention, and embodiments of the present invention are contemplated for use with any wireless communication protocol.

As mentioned, a waveform ensemble may comprise nested waveforms and/or may be composed of a plurality (e.g., 3 or more, 4 or more, 5 or more, 6 or more, 7 or more, etc.) of component waveforms combined in series to achieve a desired cognitive effect. Beneficial cognitive effects often extend in time for seconds to minutes to even hours. For instance, a state of calm or a perceived increase in energy or motivation would be most beneficial to a user if they extended for a period of time (e.g. minutes to tens of minutes or longer). To achieve cognitive effects that extend in time, waveforms may be constructed of shorter elements, including repeated elements.

A neuromodulator may apply a waveform comprising shorter waveform elements across at least two timescales to achieve extended cognitive effects. The neuromodulator may include at least one pair of transdermal electrodes in electrical communication with a controller. In general, a user may wear all or part of the neuromodulation device on his/her head such that each transdermal electrode is positionable on the head of the user. In general, the electrode number, composition, and distribution as well as the position, size, and shape of the transdermal electrodes may affect the neuromodulation received by the user. In general, the transdermal electrodes worn by the user may induce a cognitive effect of a type as described above.

The neuromodulator (neurostimulator) may include a processor that may receive waveform ensembles (or parameters describing the selected waveform ensemble) from a user device, a remote server, or other storage device. In general, the processor (controller of/in the neurostimulator) may cause delivery of waveform ensembles to a pair of transdermal electrodes and control the nested waveforms being used by the transdermal electrodes. In general, the neurostimulator may include an external, inductive, battery, or another type of power source.

The apparatuses described herein, including the control logic operating on or with the neuromodulator apparatuses, may be configured to receive, store, transmit, and in some cases analyze data from the user interactions with the apparatus. For example, the apparatus may record or take note of all or some user interactions with the apparatus, including, for example: the ensemble waveforms requested and/or played by the apparatus, one or more skin/contact readings (e.g., the skin impedance history, sampled continuously or periodically by the apparatus), requests/commands for any of the add-in effects (e.g., phosphenes, extensions, etc.), time of play of ensemble waveform, early termination, and/or user feedback (ranking, ratings, tagging, etc.), and/or information about the user (e.g., age, gender, location, etc.).

In some variations this information may be transmitted to a remote server (e.g., "cloud") for storage and/or analysis. For example, this information may be used for improving the customer experience (e.g., modifying/building ensemble waveforms based on user interaction information, including scaling information). In some variations, this information may be used to determine if a client requires one or more new components (e.g., electrodes for use with the neuromodulator), and the remote server may contact the user to offer (including with discount offers) to order or re-order additional components (e.g., particular models of electrodes).

In some variations, tracked information such as that described above may be used to provide customer support. For example, the user may be sent a message and/or advice about operation of the apparatus based on their usage; if the user is consistently terminating the delivery of the ensemble waveform early, or if the user is consistently reducing the intensity below a threshold level, or any other metric or combination of metrics, the server may initiation communication with the user (e.g., call, text, email, etc.) to provide advice/guidance. In some variations the user may opt out of this, and/or may opt out of the collection of some or all of the data described above.

In various embodiments, the user device may allow the user to control the neuromodulator such as powering the controller, running the nested waveforms, and/or controlling a transdermal electrical stimulation session. The user device may include application software running on the user computing device. The application may be operated by the user wearing the neurostimulator. The application may control the user computing device to wirelessly bi-directionally communicate with the neurostimulator by transmitting instructions to and receiving signals from the neurostimulator.

In various embodiments, the user device may be used by the user to run and/or control the neurostimulator to modify a cognitive state. In some embodiments, the waveform ensembles may be downloaded and saved into the application on the user computing device. The user device may present a plurality of waveform ensembles in a user interface to the user with the user computing device. The user device may allow the user to select a waveform ensemble from the plurality of waveform ensembles. The user device may transmit the parameters of the waveform ensemble to a controller of a neuromodulator wirelessly, for example through Bluetooth. The wireless communication may be configured to be transmitted via the Internet or other local or wide area network. Any content of wireless communication may be used, including but not limited to information relating to: diagnostics about apparatus function; battery level; TES session; user data; geolocation data; raw and/or processed data from sensors incorporated in the TES apparatus (e.g. accelerometer, EEG sensor, EMG sensor, etc.), or other information.

In general, the invention may include a non-transitory computer-readable storage medium storing a set of instructions capable of being executed by a processor in the user computing device that when executed by the processor causes the processor to allow a user to select one or more (or a set) of control parameters for controlling a neurostimulator. The set of instructions may include confirming a communication link with the neurostimulator and presenting the user with a set of waveform ensembles configured to modify the user's cognitive state. The set of instructions may include displaying, on a screen connected to the processor, a set of waveform ensembles configured to modify the user's cognitive state. In some embodiments, the set of instructions may include presenting a list and/or menu of pre-selected control values (e.g., for one or more of current amplitude, current frequency, pulse width, pulse duration, pulse frequency, pulse waveform, burst duration, burst frequency, off-time, burst waveform, positive duty cycle, negative duty cycle, amplitude modulation parameters, and on/off, etc.). The set of instructions may allow the user to select one waveform ensemble from the set of waveform ensembles. The set of instructions may permit transmission of the control values to the neurostimulator or an index to select from a list of possible predetermined waveform ensembles of such control values in the neurostimulator. The set of instructions may include transmitting the waveform ensemble parameters to the neurostimulator for application to the user's head by the neurostimulator.

Figure 5B:
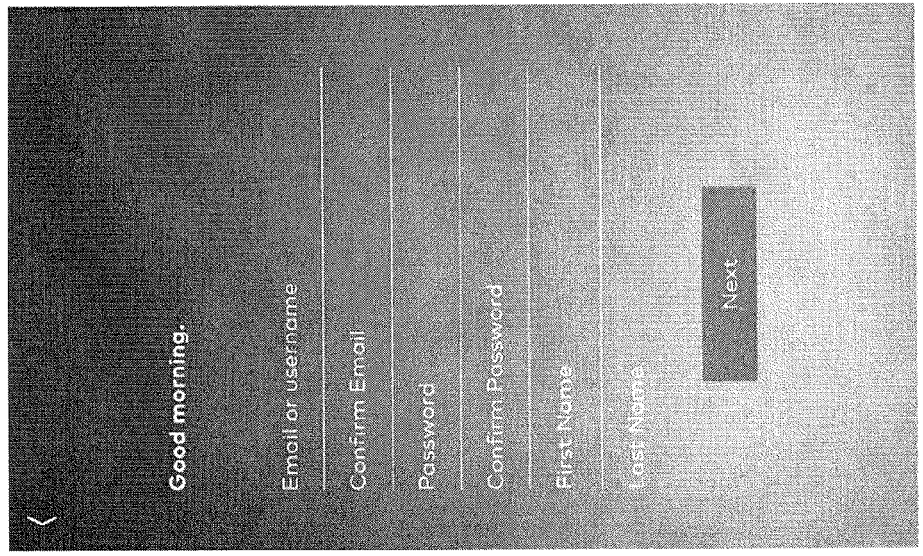
FIG. 5B illustrates a user interface that allows the user to use his/her email address as the username and select a password.
Figure 5A:
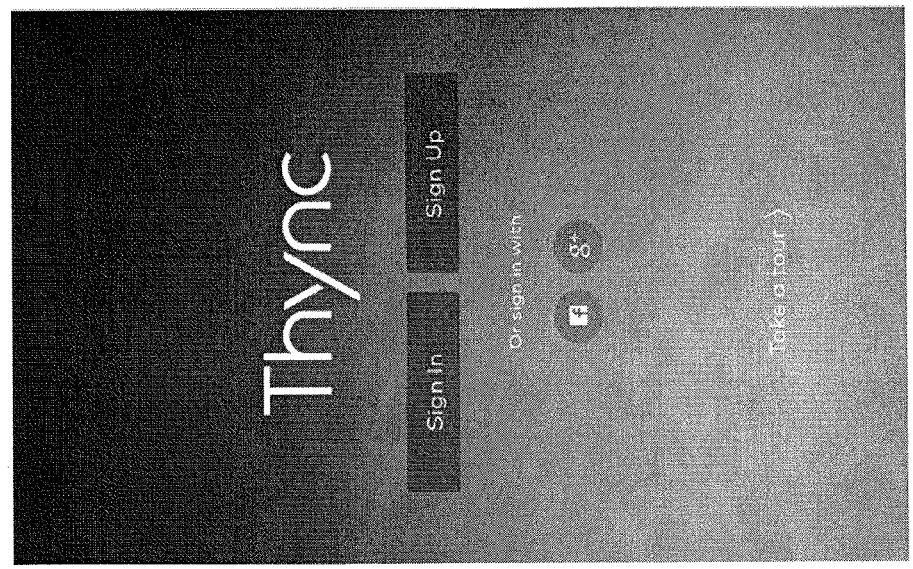
FIG. 5A illustrates a user interface that allows the user to sign up an account and sign in to the account.

In some embodiments, the user device may allow the user to sign up an account and sign in to the account as illustrated in FIG. 5A. The user device may allow the user to use his/her email address as the username and select a password as shown in FIG. 5B. The user device may allow the user to store relevant user information in the user's account.

Figure 6B:
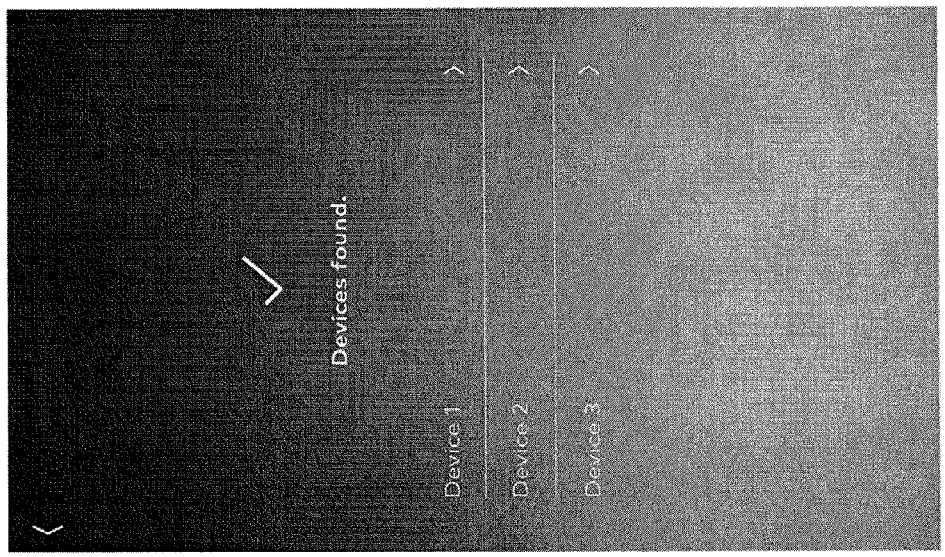
FIG. 6B illustrates a user interface that allows the user to select a neurostimulator to connect to the user computing device.
Figure 6A:
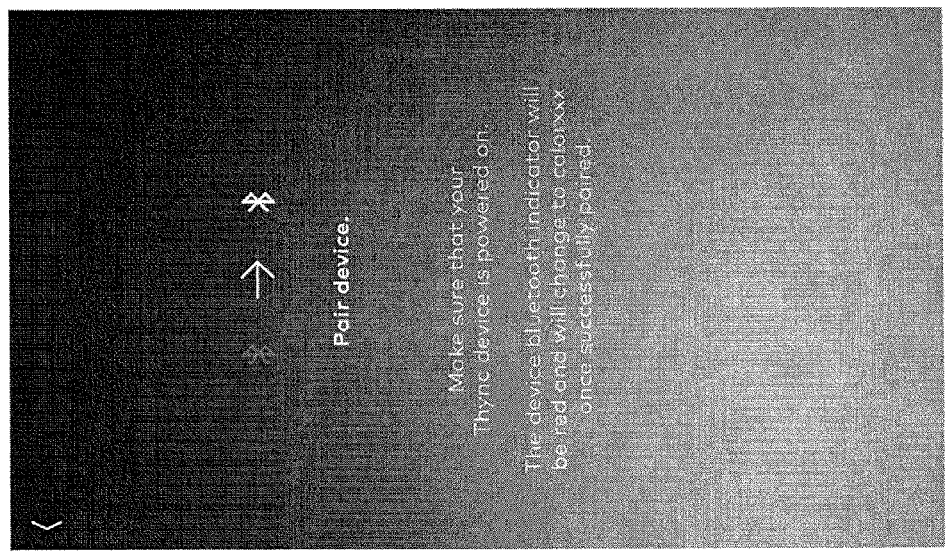
FIG. 6A illustrates a user interface that allows the user to pair the user computing device with the neurostimulator.
Figure 6D:
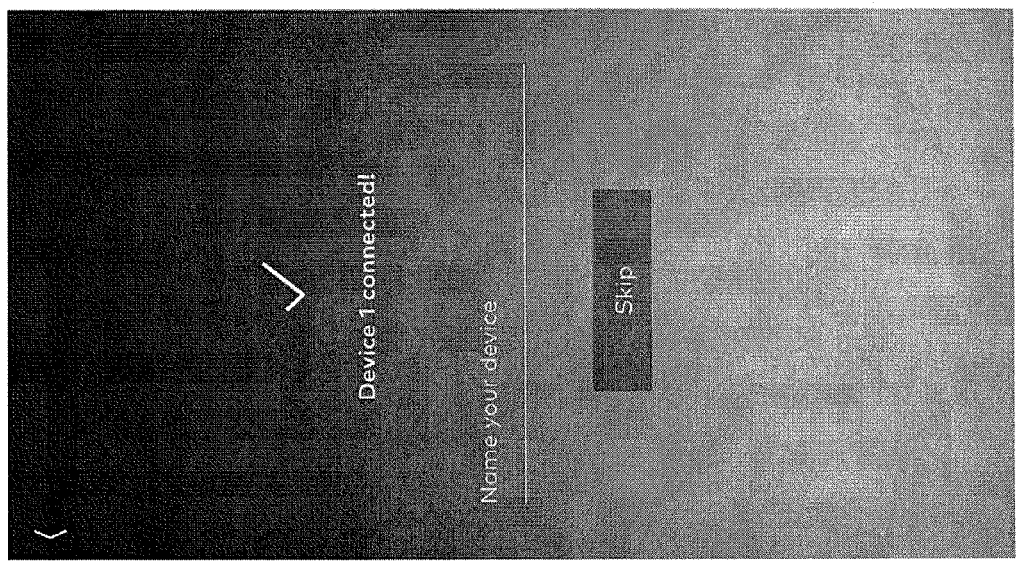
FIG. 6D illustrates that the application may inform the user when the connection is successfully established.
Figure 6C:
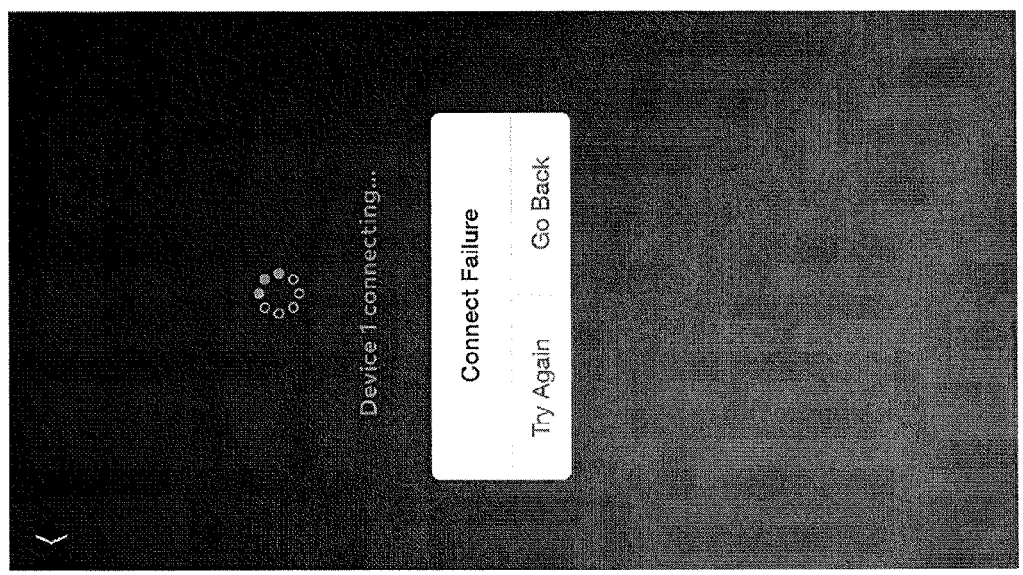
FIG. 6C illustrates that the application may notify the user when the connection is not established.

In some embodiments, the user device may allow the user to communicate with the neurostimulator bi-directionally, e.g., via Bluetooth. As shown in FIG. 6A, the user device may allow the user to pair the user computing device with the neurostimulator. The user device may search for neurostimulators within a certain range and inform the user after the neurostimulators are found as shown in FIG. 6B. After the user device locates the neurostimulator, the user device may try to establish connection between the neurostimulator and the user computing device. FIG. 6C illustrates that the user device may notify the user when the connection is not established. FIG. 6D illustrates that the user device may inform the user when the connection is successfully established. The user device may allow the user to name the neurostimulator, or to skip naming and proceed directly to commence and control the neurostimulation session.

In some embodiments, the user device may also allow the user to confirm that the electrodes are applied. The user device can be configured to allow the user computing device to detect whether the electrodes are applied. In some embodiments, the neurostimulator can be configured to have an element that indicates whether the electrodes are applied, and in which configuration the electrodes are applied. For example, in one embodiment, the neurostimulator can be configured to have a capacitor, where the current of the capacitor can be zero when the electrodes are not applied, and the current of the capacitor after the electrodes are applied can indicate whether the electrodes are in a "calm" configuration as illustrated in FIG. 1C, in "energy" configuration as illustrated in FIG. 1A, or in "energy" configuration as illustrated in FIG. 1B. In some other embodiments, the electrical parameter such as current, voltage or resistance in some other element can be used to detect whether the electrodes are applied and the configuration of the electrodes.

Figure 7:
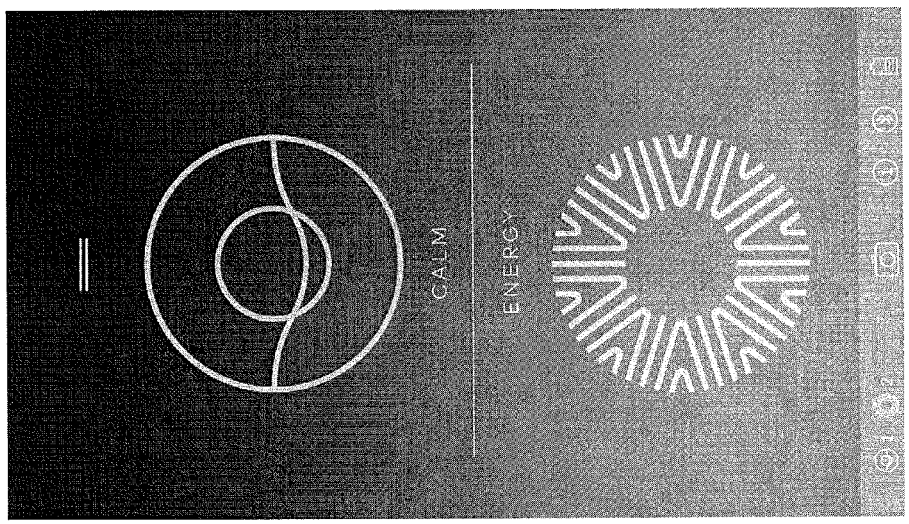
FIG. 7 illustrates a user interface presenting the subsets of various cognitive effects in accordance with one embodiment of the invention.

FIG. 7 illustrates a user interface presenting the subsets of various cognitive effects in accordance with one embodiment of the invention. In various embodiments, the waveform ensembles for modifying the cognitive state may be downloaded and saved into a library (i.e. database) of the application on the user computing device. The waveform ensembles may be divided into different subsets, for example, "calm" or "energy". The waveform ensembles in the subset of "calm" can be designed to have a calming effect on the user. On the other hand, the waveform ensembles in the subset of "energy" can be designed to make the user feel more energetic, aroused, and focused.

In some embodiments, the user device may allow the user to select a subset of waveform ensembles in a desired cognitive state, for example, calm or energy, as illustrated in FIG. 7. In some other embodiments, after the user device detects the configurations of the applied electrodes, the user device may take the user directly to the user interface presenting a plurality of waveform ensembles in the corresponding subset of cognitive effect. For example, after the user device detects the applied electrodes are in "calm" configuration as illustrated in FIG. 1C, the user device may take the user directly to the user interface presenting a plurality of waveform ensembles in subset of "calm" effect. Thus the user device may skip the user selecting the subset of cognitive effect step.

In some embodiments, the user device may help the user to apply the electrodes of the neurostimulator to the proper positions of the body of the user. The user device may show a movie to give a tutorial about how to apply the electrodes in different configurations to achieve corresponding cognitive effects. For example, as shown in FIG. 7, the user device may allow the user to see a movie with a tutorial (or other, more static, instructions) about how to apply the electrodes properly by clicking on the small icon with a letter "i" at the bottom of the screen.

In some embodiments, the user device may be configured to allow the user to use the camera of the user device to help with the proper positioning of the electrodes of the neurostimulator. For example, the user device may allow the user to see a "mirror" (front facing camera) by pressing on the small camera icon at the bottom of the screen, as illustrated in FIG. 7. After the user presses on the camera icon, the user device may turn on the camera function of the user device to help the user to properly place the electrodes in the desired positions. In some embodiments, the user device may allow the user to capture video by pressing the camera button to assist the user in positioning an electrode. For example, the user device may display real-time video or camera pictures on the screen in a 'mirror mode' (front-facing mode) while the user places electrodes. Moreover, the user device may incorporate a visual guide about the configuration shown on the screen along with the real-time video or camera pictures. In another embodiment, a computer vision algorithm uses fiduciary landmarks on a user's face or head in an 'augmented reality' framework so that an electrode configuration is layered on the video or camera picture to provide feedback for the user about electrode positioning. The user device may capture still or video images from the front-facing camera for automated or manual analysis in order to provide the user feedback about device positioning.

The set of instructions stored in the non-transitory storage medium may also include instructions and/or guidance for applying the device (e.g., both primary and secondary electrode regions) to the proper positions on the body. For example the set of instructions executable on the processor of the user computing device may include displaying one or more diagrams indicating where on the user to position the first and second electrodes of the neurostimulation device. The set of instructions may include playing a movie illustrating how to apply the neurostimulator electrodes. The set of instructions may also include showing a mirror by using the camera of the user device to help with the proper positioning of the electrodes of the neurostimulator.

Figure 8B:
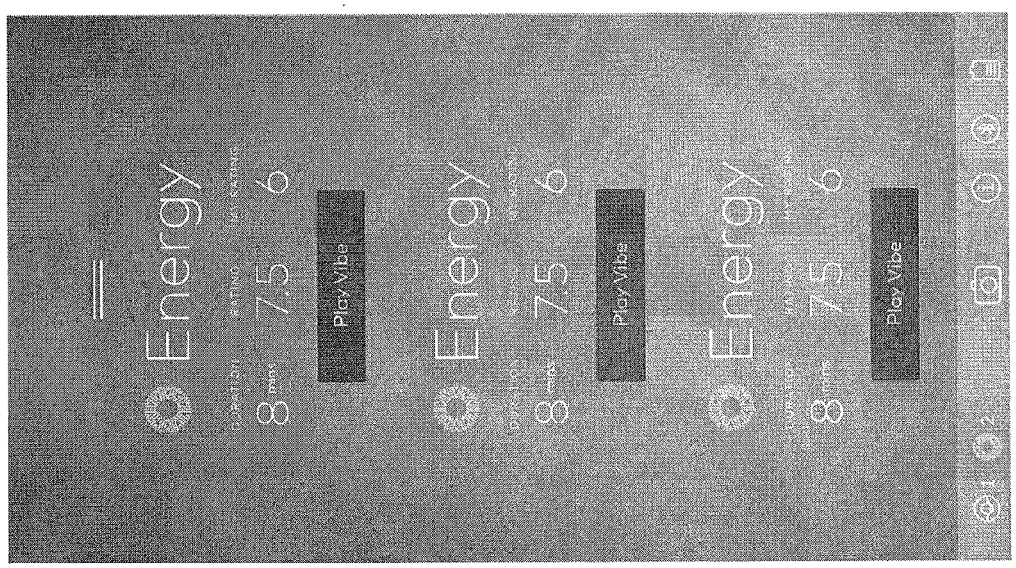
FIG. 8B illustrates an example of the user interface of the application presenting a plurality of waveform ensembles in the subset of "energy" according to some embodiments of the invention.
Figure 8A:
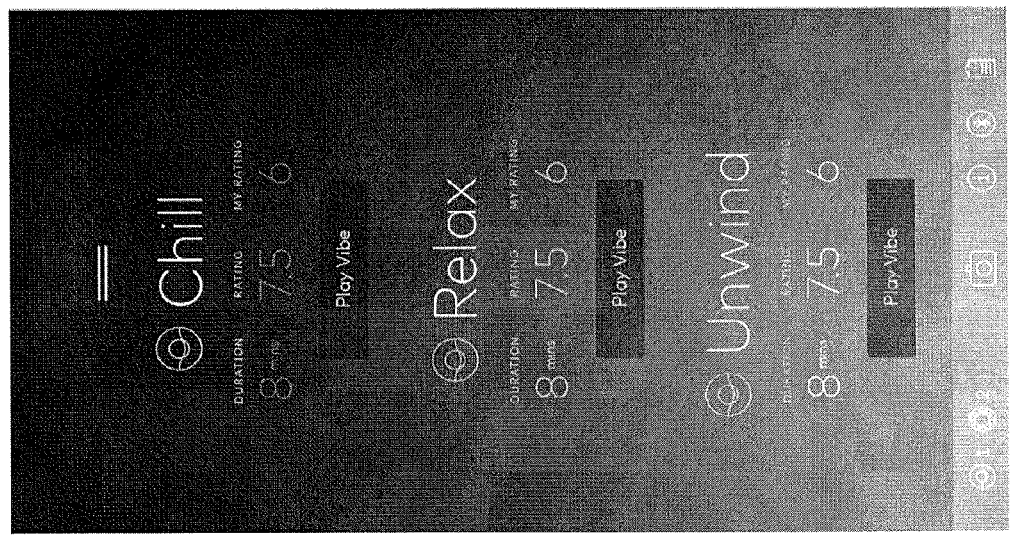
FIG. 8A illustrates an example of the user interface of the application presenting a plurality of waveform ensembles in the subset of "calm" according to some embodiments of the invention.

FIG. 8A and FIG. 8B illustrate examples of the user interfaces of the user device presenting a plurality of waveform ensembles in the subsets of "calm" and "energy" respectively according to some embodiments of the invention. The user device may present a plurality of waveform ensembles in the library to the user. The user device may allow the user to select a specific waveform ensemble from the plurality of waveform ensembles. Selection of a waveform ensemble indicates that the user wants to run that particular waveform ensemble during a transdermal electrical stimulation session. For example, the user device may present a list of various waveform ensembles as shown in FIG. 8A and FIG. 8B. The user device may present the user the duration, the average rating, and the user rating of the waveform ensembles. The user may select the waveform ensemble by pressing on "Play Vibe", where "Vibe" is a short notation for "waveform ensemble".

Figure 8C:
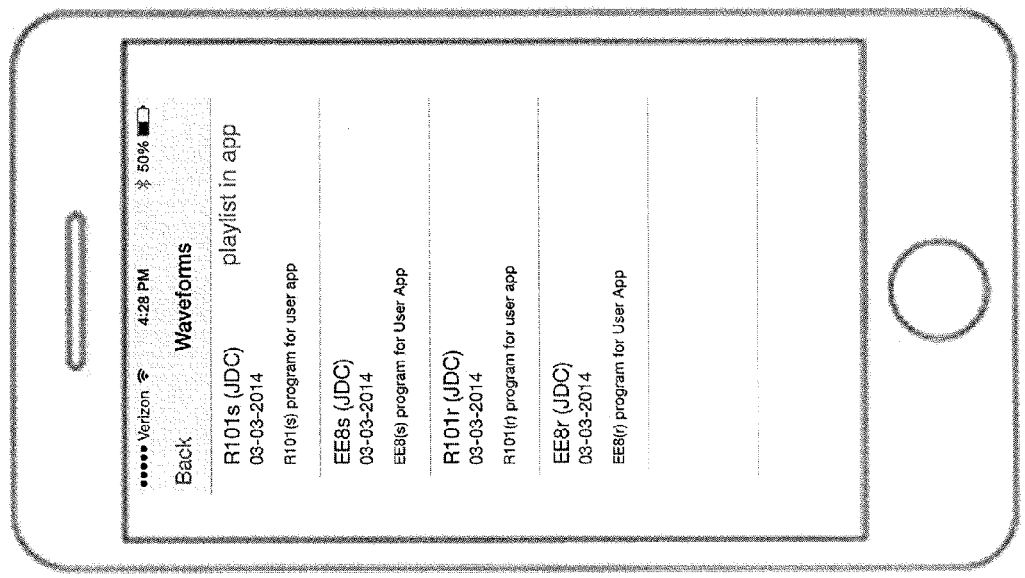
FIG. 8C illustrates an example of the user interface of the application presenting a plurality of waveform ensembles as a playlist.

FIG. 8C illustrates another example of the user interface according to another embodiment. The user device may present the user a "playlist" in the user interface. Selection of a waveform ensemble from the "playlist" indicates that the user wants to run that particular waveform ensemble during a transdermal electrical stimulation session.

The user device may present the plurality of waveform ensembles in the library to the user in various forms including, but not limited to a list, a table, a map, or other various forms. The user device may also provide personalized waveform ensembles in some embodiments. For example, the user device may provide diagnosis by asking the user a set of questions. The user device may recommend waveform ensembles according to the answers from the user. The user device may create a user profile using the answers from the diagnosis questions. The recommended waveform ensembles can be personalized waveform ensembles selected and/or designed by analyzing the user profile.

The user device may transmit the user selected waveform ensemble parameters or index wirelessly to the neurostimulator. After the user device allows the user to select the specific waveform ensemble, the user device may communicate with the neurostimulator and instruct the neurostimulator to apply the specific waveform ensemble the user selected. The user device may transmit the control parameters of the specific waveform ensemble to the neurostimulator in some embodiments. The user device may transmit the index of the specific waveform ensemble to the neurostimulator in some other embodiments.

In some embodiments, the user device may wirelessly and periodically transmit waveform ensemble parameters from the user device to the neurostimulator in chunks during a stimulation period. The user device may transmit waveform ensemble parameters to the neurostimulator at a first time interval during the stimulation period. For example, the first time interval may be 100 ms, 200 ms, 300 ms, 400 ms, 500 ms, 600 ms, 700 ms or 800 ms or any values therebetween. The values outside the above range may also be possible. Alternatively, the first time interval may be very short so that waveform ensemble parameters are transmitted in real-time or near real-time, for example by using an interval of less than 100 ms (i.e. less than 50 ms; less than 25 ms; less than 10 ms; less than 5 ms; or less than 1 ms). The neurostimulator may be configured to transmit a confirmation signal, for example, a heart beat, at a second time interval. The second interval may be less than the first time interval. In some embodiments, the user device may instruct the user computing device to stop transmission of the waveform ensemble parameters if the confirmation signal is not received by the user device.

Figure 9B:
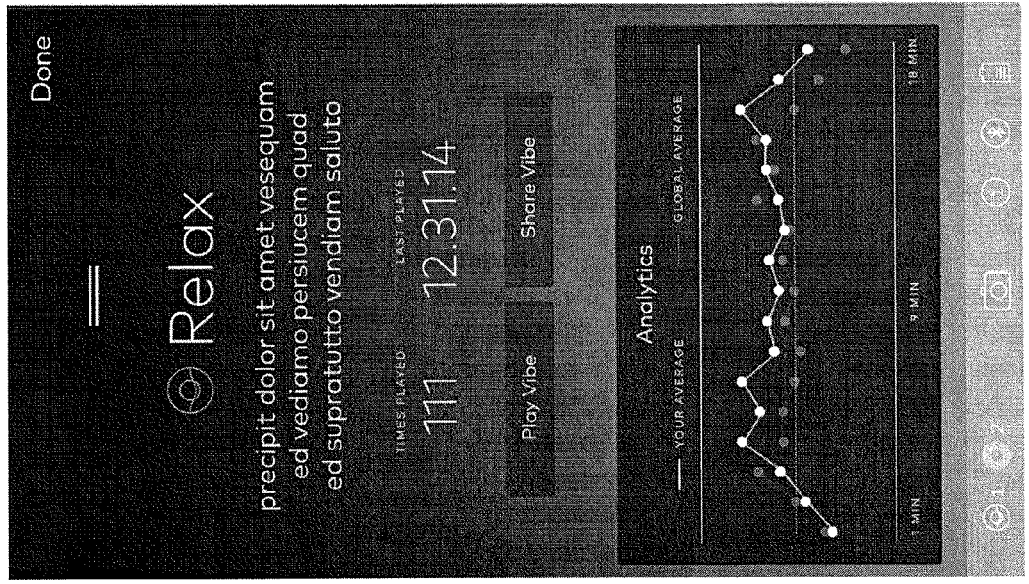
FIG. 9B illustrates an example of the user interface presenting the user's history of using the neurostimulator with a particular ensemble waveform.
Figure 9A:
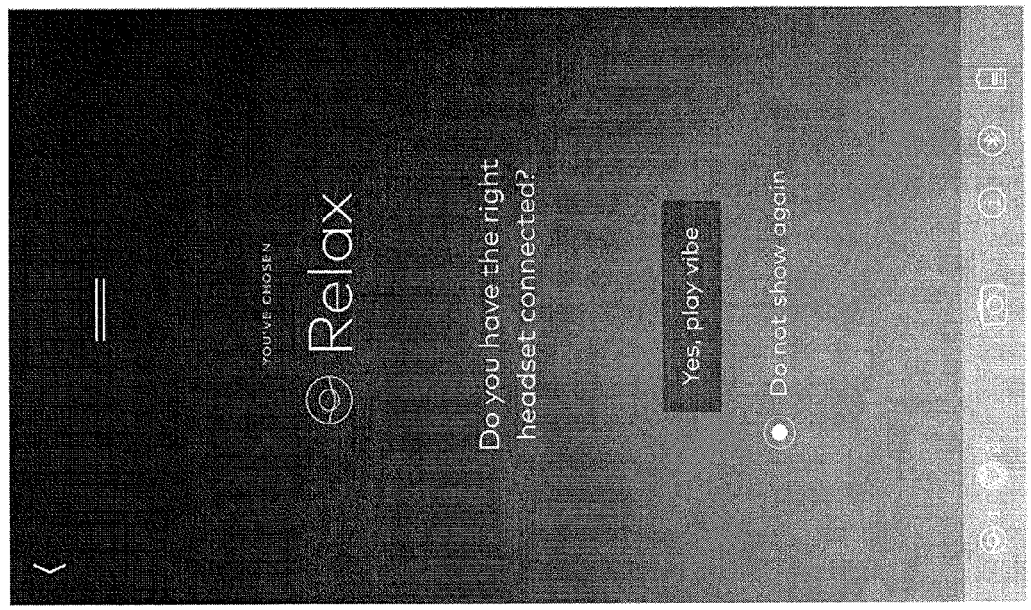
FIG. 9A illustrates an example of a user interface that reminds the user to check whether the headset (electrode assembly) is properly connected.

Before running the specific waveform ensemble that the user selected for the neurostimulation session, the user device may remind the user to check whether the headset (i.e. electrode apparatus) is properly connected as shown in FIG. 9A. In some variations, the electrode type may be automatically detected, and only waveforms appropriate for that electrode set and cognitive effect are displayed for user selection. As discussed above, different configurations of the electrodes may result in different cognitive effects. It is important for the user to use the proper electrode assembly with the electrodes in the proper configuration in order to comfortably receive a significant cognitive effect. The user device may also keep a record of the user's history of using the neurostimulator including the configurations of the electrodes applied, the waveform ensembles selected, the total times the user has played the specific waveform ensemble, the last time the user played the waveform ensemble, the global average rating of all users (or a subset of users selected according to a demographic, psychographic, or geographic categorization); and the user's rating of the waveform ensemble, etc. FIG. 9B illustrates an example of a user interface presenting the user's history of using the neurostimulator. As shown in FIG. 9B, the user device may present analytics of user data. For example, the analytics may include history of the user's experience using the specific waveform ensemble including when a waveform was used (i.e. timeline), as well as ratings for effect and/or comfort. The analytics may indicate the perceived intensity during the TES stimulation session the user has selected via the controls which will be discussed below.

Figure 10B:
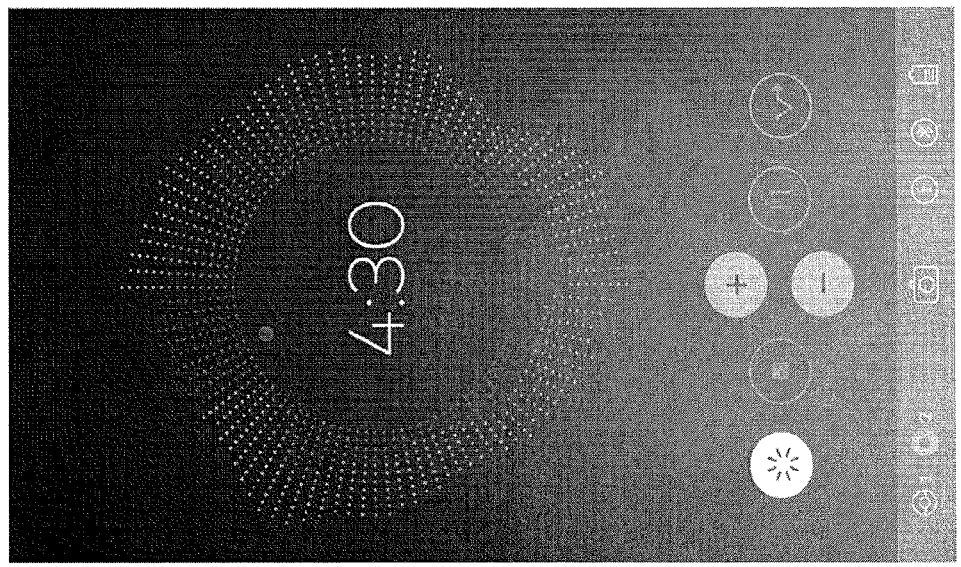
FIG. 10B illustrates another example of the user interface allowing the user to control the applied waveform ensemble during application of the waveform ensemble according to some embodiments of the invention.
Figure 10A:
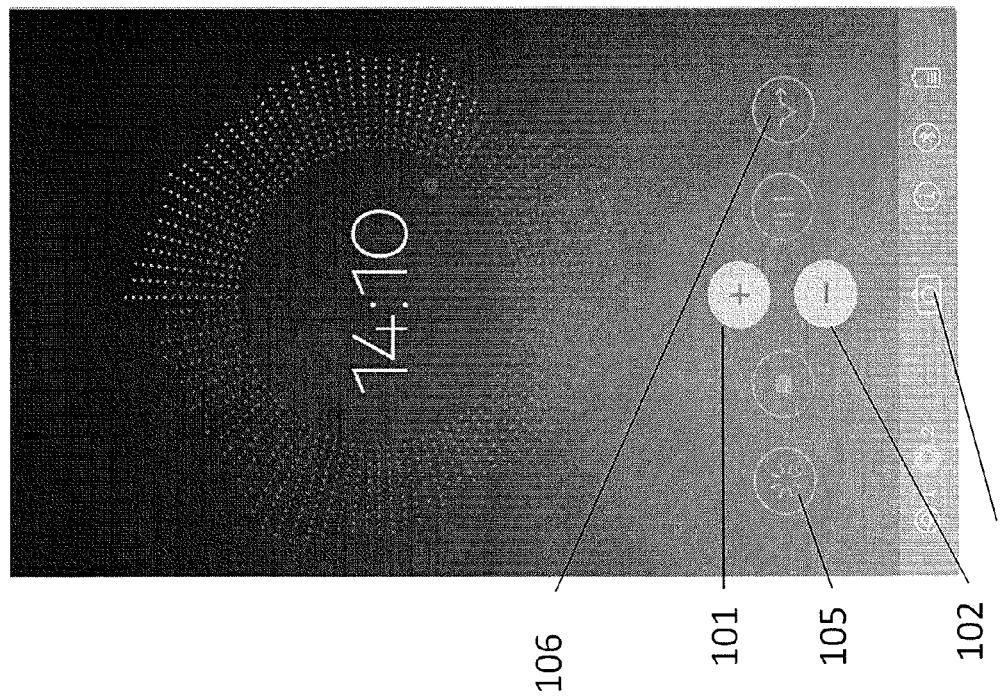
FIG. 10A illustrates an example of the user interface allowing the user to control the applied waveform ensemble during application of the waveform ensemble according to some embodiments of the invention.
Figure 10C:
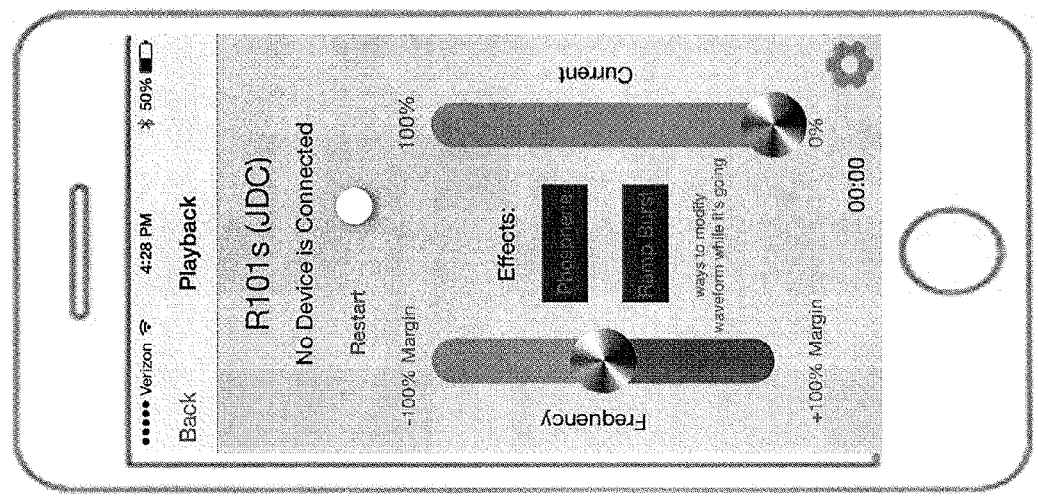
FIG. 10C illustrates yet another example of the user interface allowing the user to control the applied waveform ensemble during application of the waveform ensemble according to some other embodiments of the invention.

FIG. 10A, FIG. 10B and FIG. 10C illustrate examples of user interfaces allowing the user to control the applied waveform ensemble during application of the waveform ensemble according to some embodiments of the invention. In various embodiments, the user device can allow the user to control the applied waveform ensemble with the user device during application of the waveform ensemble. For example, when the user activates the user interface by clicking on an icon, pushing a physical button, switch, or the like, the delivery of the waveform ensemble may start, pause, stop, or be modulated (e.g. a parameter of a TES waveform be changed).

In various embodiments, the non-transitory computer-readable storage medium storing a set of instructions capable of being executed by the processor of the user computing device, causes a user interface for commencing a waveform ensemble to be displayed on the screen of the computing device, and enables a control connected to the processor. The set of instructions may include allowing modification of one or more of these control parameters of the applied waveform ensembles. The user may adjust the control to modify the applied waveform ensemble during application of the waveform ensemble. The set of instructions may include allowing the user to adjust the perceived intensity of the applied waveform ensemble during application of the waveform ensemble.

FIG. 10A illustrates one example of the user interface on a user computing device for controlling and/or changing a waveform ensemble during a transdermal electrical stimulation session. In some embodiments, the user interface may include at least one interactive component for modulating at least one element within the waveform ensemble. In some embodiments, a user may modulate a waveform ensemble before and/or during a transdermal electrical stimulation session. In some embodiments, a user may modulate the intensity, frequency, amplitude, duration, ramping, pulse length, peak current, percent duty cycle, amplitude modulation parameters, or percent charge imbalance of a TES waveform ensemble. In some embodiments, the user device may allow the user to adjust the overall cognitive effect during the neurostimulation session by adjusting the perceived intensity of the applied waveform ensemble with the user device during application of the waveform ensemble. The perceived intensity can be used to represent the overall cognitive effect the user perceived from the applied waveform ensemble. The perceived intensity may result from a combination of the waveform parameters including current, frequency, duty cycle, amplitude modulation parameters (amplitude modulation frequency, amplitude modulation waveform, amplitude modulation duty cycle, etc.) and percent charge imbalance. For example, the perceived intensity may be calculated by the following equation:

$$\text{Perceived Intensity} = \text{Current} \times (11000/\text{Frequency}) \times (0.5 + \text{charge imbalance percentage}/200) \times (\text{Duty Cycle}/100)$$

As illustrated in FIG. 10A, the user device may allow the user to modulate the applied waveform ensembles by including a control to allow a percentage (0%-100%) of the perceived intensity to be applied in some embodiments. The user device may allow the user to control the neurostimulator by adjusting the perceived intensity to control the overall cognitive effect. The non-transitory computer-readable storage medium storing a set of instructions capable of being executed by the processor of the user computing device, may cause the user interface to allow the user to adjust the perceived intensity of the applied waveform ensemble during application of the waveform ensemble. The set of instructions may also allow the subject to turn the device on/off.

The user device may allow the user to increase the perceived intensity gradually by pressing the icon 101 with the '+' sign. The increase of the perceived intensity can be gradual with small steps to ensure the safety and comfort of the user. On the other hand, the time delay for increased perceived intensity cannot be too large. Otherwise, the user may increase the intensity by several increments without feeling the change in intensity on the skin, thus causing safety concerns by increasing the likelihood a user will increase intensity too far too quickly without the benefit of feedback on the perceived intensity change via skin sensations. For example, the increase of the perceived intensity may be between from 0.01 mA per second to 1 mA per second. The values outside the above range may also be possible. For example, particular 'add-in' effects, represented by buttons that can be pressed by a user and which induce a phosphene 105 or cause a transient change in the intensity of the electrical stimulation to enhance the induced cognitive effect 106 may trigger changes in intensity greater than 1 mA/second The user device may allow the user to decrease the perceived intensity or end the TES neurostimulation session quickly. When the user may feel uncomfortable or pain, or some problems with the electric circuits of the TES neurostimulator, the user device can allow the user to reduce the perceived intensity by pressing the icon 102 with the "−" sign (for example, to press the icon 102 repeatedly to reduce the perceived intensity by a large amount) or end the waveform ensemble by pressing the "pause" button (icon with two parallel lines) or "stop" button (icon with a square). In some embodiments, the user device may allow the user to decrease the perceived intensity or end the TES neurostimulation session instantaneously. In some embodiments, the user device may allow the user to decrease the perceived intensity or end the TES neurostimulation session relatively quickly but with a time period such that the user will not feel pain because of a sudden decrease of the perceived intensity (i.e. the intensity of stimulation may gradually ramp down over five seconds). For example, the decrease of the perceived intensity may be between from 0.5 mA per second to 10 mA per second. The values outside the above range may also be possible.

FIG. 10C illustrates another embodiment of the user interface on a user computing device for controlling a waveform ensemble during a transdermal electrical stimulation session. In some embodiments, the user may modulate the intensity, frequency, amplitude, duration, ramping, pulse, peak current, percent duty cycle, amplitude modulation parameter, or percent charge imbalance of the waveform ensemble. In some embodiments, as shown in FIG. 10C, the interactive component may include a virtual dial, slider, button, joystick, dropdown menu, data entry field, and/or any other type of interactive component. For example, the frequency and current may be increased or decreased by sliding a virtual slider up or down. In some variations, the user interface may include one control that changes two or more parameters at once (e.g., frequency and peak intensity, which may be both increased/decreased together, or in any other relationship, e.g., increasing frequency while decreasing intensity or vice versa).

In some embodiments, the user interface may include a "restart" slider, timer, connection status banner, and other indicators (e.g. play/pause set of buttons). In some embodiments, the "restart" slider may be used to restart a transdermal electrical stimulation session. In some embodiments, the user interface may indicate to the user the status of a connected device. For example, the connected status banner may indicate that a controller, a pair of transdermal electrodes, or another device is connected. In another example, the connected status banner may indicate the battery charge status of a controller. In some embodiments, the connection may be a hardwired connection or a wireless connection. In some embodiments, software may be configured to continuously check a wireless connection status between the neuromodulation device and the controller, the computing device, or any other type of device.

Any of the variations described herein may allow a user to extend an ongoing (or just ended) ensemble waveform for an additional amount of time. For example, a control (e.g., button, slider, etc.) may be present on the user interface or may appear when nearing the end of the delivery time of the ensemble waveform (or immediately after an ensemble waveform completes). This button or slider may then be selectable to allow the user to add additional time (add additional ensemble waveform duration) onto the ongoing ensemble waveform. The added waveforms may replicate one or more of the previous component waveforms (e.g., the component waveforms forming the last x minutes of the ensemble waveforms, where the last x minutes refers to the amount of time sought to be added by the extension, e.g., x may be between 30 seconds and 1 hour (e.g., 30 seconds, 1 minute, 2 minutes, 3 minutes, 4 minutes, 5 minutes, 6 minutes, 7 minutes, 8 minutes, 9 minutes, 10 minutes, 15 minutes, 20 minutes, etc.). The apparatus may allow unlimited extension of the time, or it may limit the number of extensions to some number (e.g., 1, 2, 3, 4, 5, 6, 7, 8, 9, 10, etc.). This may be referred to as a "vibe" extension or play extension (or ensemble waveform extension).

As mentioned, in some variations a notification and/or control (e.g., button, etc.) may become visible and/or available near the end of a waveform ensemble delivery time. The user may also be prompted to extend and/or asked if they would like to extend the session. For example, when running an ensemble waveform having a 10 minute duration, when there is still time left (e.g., 5 minutes, 4 minutes, 3 minutes, 2 minutes, 1.5 minutes, 60 seconds, 30 seconds, 15 seconds, etc.) the apparatus (e.g., a user interface) may ask the user whether they want to add addition time (e.g., 5 minutes) to the session. If they select/approve the extension then additional component waveform(s) are added to the end of the waveform without the delivery stopping. This may be particularly useful when the user has selected an appropriate intensity and is habituated to the skin sensations so that they can feel a stronger effect (e.g., calm or energy effect), which will be more fully experienced by an extended waveform.

Referring to FIGS. 10A, 10B and 10C, the user device may allow the user to control the neurostimulator to trigger pre-determined signals including, but not limited to phosphenes, an intensifier (i.e. a brief (less than 20 seconds, optimally less than 10 seconds) modulation of one or more ensemble waveform parameter (generally to transiently increase then transiently decrease; or transiently decrease then transiently increase the intensity of stimulation)), or any other signals. In some embodiments, the user may introduce a phosphene protocol during a transdermal electrical stimulation session. As shown in FIG. 10A, a phosphene protocol or ramp burst may be initiated by the user selecting a virtual button (i.e. a button on a user interface of a user computing device). The user interface may restrict the timepoints during a TES session when a user may select waveform modulator such as a phosphene protocol or ramp burst may be restricted. By restricting the timepoints when a modulator may be triggered, the system may only permit the user to trigger a modulator signal when it will be appropriately comfortable and/or effective. In some embodiments, the user device may include instructions to guide the placement of electrodes for reliably generating phosphenes. The user device may also allow the user to trigger the intensifier. The intensifier may allow the user to have an intensified experience by transiently decreasing then increasing the applied waveform intensity or by transiently increasing then decreasing the applied waveform intensity. The user device may allow the user to trigger any predetermined signals in various embodiments. The non-transitory computer-readable storage medium storing a set of instructions capable of being executed by a processor, may, when executed by the processor, cause the processor to instruct the neurostimulator to trigger pre-determined signals including, but not limited to phosphenes, an intensifier or any other signals.

Burst stimulation, a form of amplitude modulation wherein bursts of high frequency (>750 Hz) pulsed TES are delivered with intervening pauses of stimulation, is an effective waveform for inducing phosphenes when the frequency of bursts (i.e. inverse of inter-burst period) is less than 100 Hz (optimally between about 8 Hz and about 70 Hz).

In some embodiments, the user device may display a representation of the perceived intensity of a waveform ensemble to be delivered on the user device. This may be shown alongside or overlaid with the user adjusted perceived intensity of the waveform ensemble, which may be the perceived intensity actually applied by the neurostimulator. In some embodiments, the running display is shown as an annular display as illustrated in FIG. 10A and FIG. 10B (and again in FIG. 10D).

In general, the user device may display a representation of the perceived intensity of a waveform ensemble to be delivered so that the user can visualize both the progression though the ensemble waveform and an estimate of the perceived intensity. For example, the user device may display an instantaneous peak perceived intensity of a waveform ensemble for a plurality of time intervals. As discussed above, the user device may allow the user to increase or decrease the perceived intensity of the waveform ensemble by pressing the increasing button 101 or the decreasing button 102 as the waveform ensemble is applied to the user. These user controls (buttons, dials, sliders, knobs, etc.) may be virtual (e.g., on a touchscreen) or they may be solid-state controls on the user device. The control(s) may be preset to a middle value (e.g., 50% of the maximum or peak perceived intensity set by the ensemble waveform) which may be adjustable up or down (e.g., up to 100% of the peak perceived intensity set by the ensemble waveform or down to 0%, or off). Alternatively, the control(s) may be preset to a value personalized for a user based on previous use of the selected ensemble waveform, other similar ensemble waveforms, or other information about the user (sex, age, skin quality, risk preference, etc.) The control may be indicated as a percent, or not. For example, the user may adjust the perceived intensity of the waveform ensemble being applied by the neurostimulator by selecting a percentage for the perceived intensity from a control on the user device. The user device may display the user adjusted perceived intensity over the representation of the perceived intensity of the waveform ensemble to be delivered. For example, the user device may display the user adjusted perceived intensity in a different color over the representation of the perceived intensity to be delivered for each time interval. FIG. 10B illustrates the running overlay display as the TES neurostimulation session progresses. In some other embodiments, the running overlay display may include a waterfall display. The running display may include a chart, a list, a map, a table or any other form of overlay displays. The user device may allow the user to adjust the perceived intensity and record the user adjusted perceived intensity, which might allow the user or an automated system to create personalized waveform ensembles to achieve individualized cognitive effect.

Figure 10E:
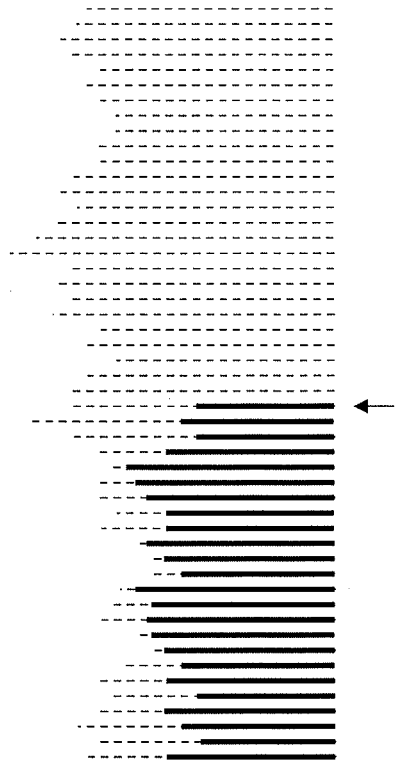
FIG. 10E is another example of display showing the maximum perceived intensity of a waveform ensemble to be delivered by the neurostimulator device (dotted lines) with the adjusted applied perceived intensity (solid lines) represented on top of the maximum perceived intensity; the maximum perceived intensities are represented as a row of lines or bars.
Figure 10D:
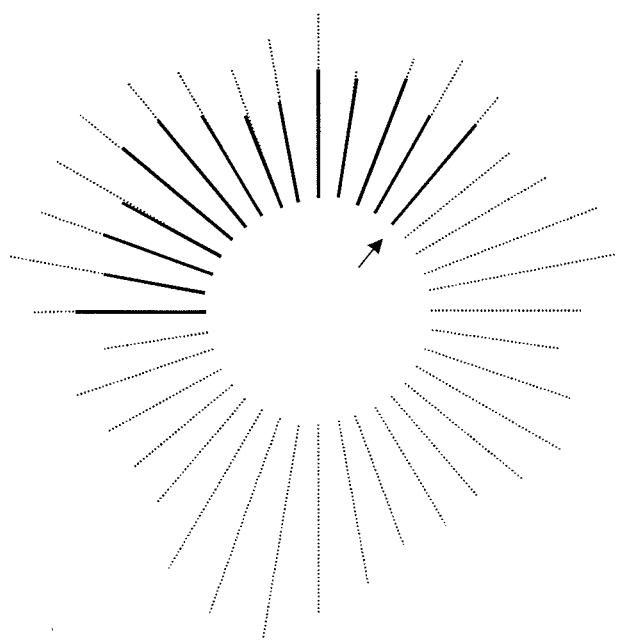
FIG. 10D is another example of a display (similar to that shown in FIGS. 10A and 10B) illustrating the display of the maximum perceived intensity of a waveform ensemble to be delivered by the neurostimulator device (dotted lines) which also shows the adjusted applied perceived intensity (solid lines); the maximum perceived intensities are represented as a circular arrangement of bars, with the time left for the waveform ensemble shown in the center.
Figure 10G:
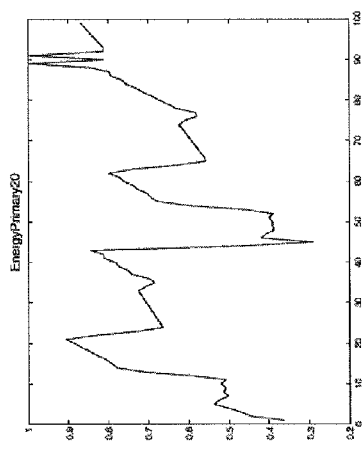
FIGS. 10F and 10G illustrate one variation of a display of the maximum perceived intensity for one variation of an ensemble waveform as a radial display (FIG. 10F) and a graphical display (FIG. 10G) after dividing it up into 100 equal time periods. The user-modified or adjusted perceived intensity may be plotted on top of these displays. This variation of an ensemble waveform is a 20 minute long "energy" ensemble waveform.
Figure 10I:
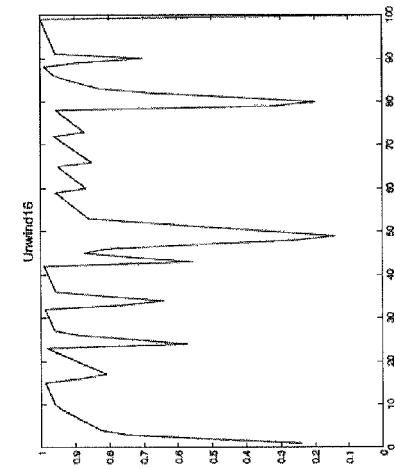
FIGS. 10H and 10I illustrate another variation of a display of the maximum perceived intensity for one variation of an ensemble waveform as a radial display (FIG. 10H) and a graphical display (FIG. 10I) after dividing it up into 100 equal time periods. The user-modified or adjusted perceived intensity may be plotted on top of these displays. This variation of an ensemble waveform is a 16 minute long "calm" ensemble waveform.
Figure 10F:
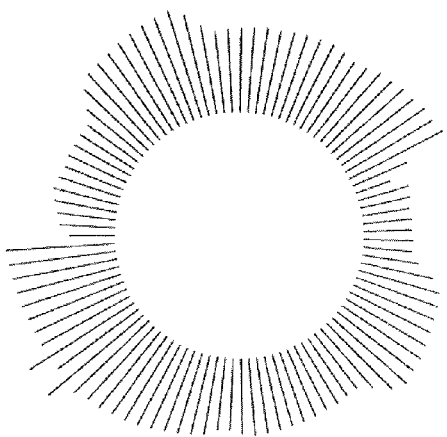
Figure 10H:
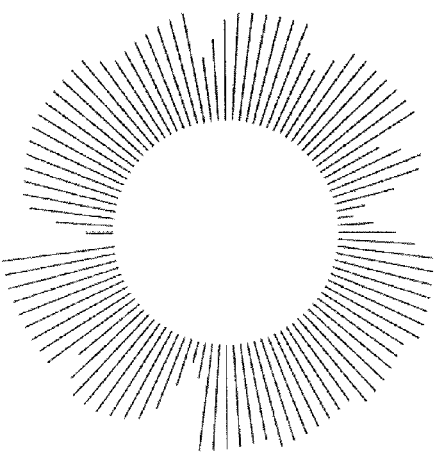

FIGS. 10D and 10E also illustrate an example of the display showing both the maximum (or target) perceived intensity of the ensemble waveform (shown as dotted lines in FIG. 10D, and dashed lines in FIG. 10E), as well as the adjusted perceived intensity shown as solid, thicker lines in FIGS. 10D and 10E, which are overlaid onto the dashed lines representing the maximum/peak perceived intensity. In this example, the perceived intensity is calculated as a combination of the values of the waveform parameters, including frequency, current amplitude (referred to as intensity, which is distinguished from the perceived intensity, which may, but does not have to, include one or more other waveform parameters), percent charge imbalance, amplitude modulation parameters, and duty cycle, etc. FIG. 10D shows the maximum perceived intensity for the complete waveform ensemble as a radial/annular graph, with the user's current place in the delivered waveform indicated by an arrow (which may be a dot, as in FIGS. 10A and 10B, or any other symbol—or indicated by the presence of colored or filled positions on the perceived intensity representation). In FIG. 10E, the maximum perceived intensity for the ensemble waveform and user-adjusted perceived intensity is shown as a linear arrangement. In some variations this may be shown as a line graph rather than the bar-type graphs shown in FIGS. 10D and 10E. Other arrangements are possible. FIGS. 10E-10G and 10H-10I illustrate two other examples of maximum or peak perceived intensities for two types of ensemble waveforms (energy in FIGS. 10E-10G and calm in FIGS. 10H-10I). Although it may be particularly helpful to show a representation of the entire peak/maximum perceived intensity for the duration of the ensemble waveform, in some variations it may be desired to show only a smaller window, which may be updated as a moving window and/or waterfall-type display (not shown). These displays may also show other features, including when the user selects a control such as the intensifier 106 (e.g., a ramp burst) or phosphene 105 to trigger these events. As shown in FIGS. 10A and 10B, the display may also include a display of the time remaining and/or the time the waveform has been running.

Figure 11B:
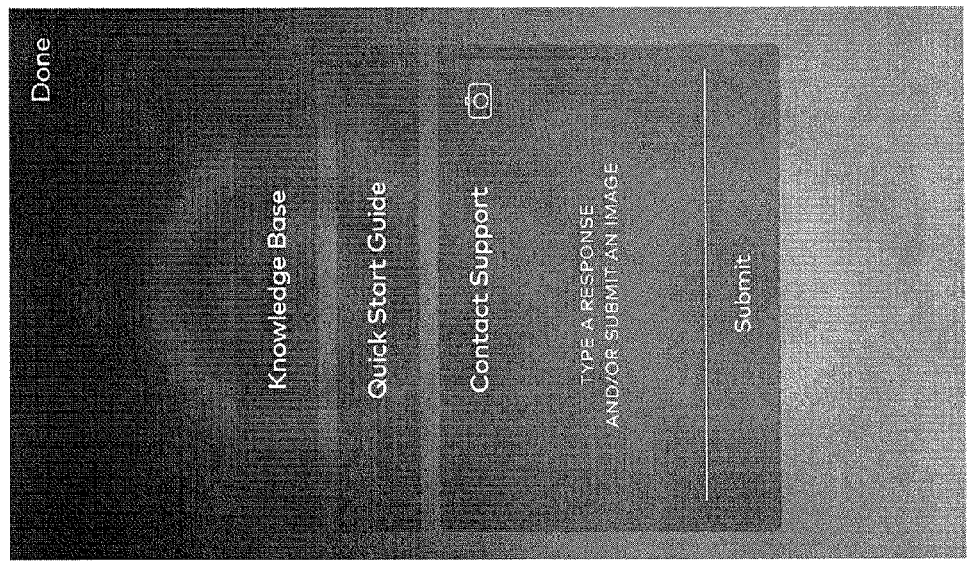
FIG. 11B illustrates a user interface that allows the user to submit a response.
Figure 11A:
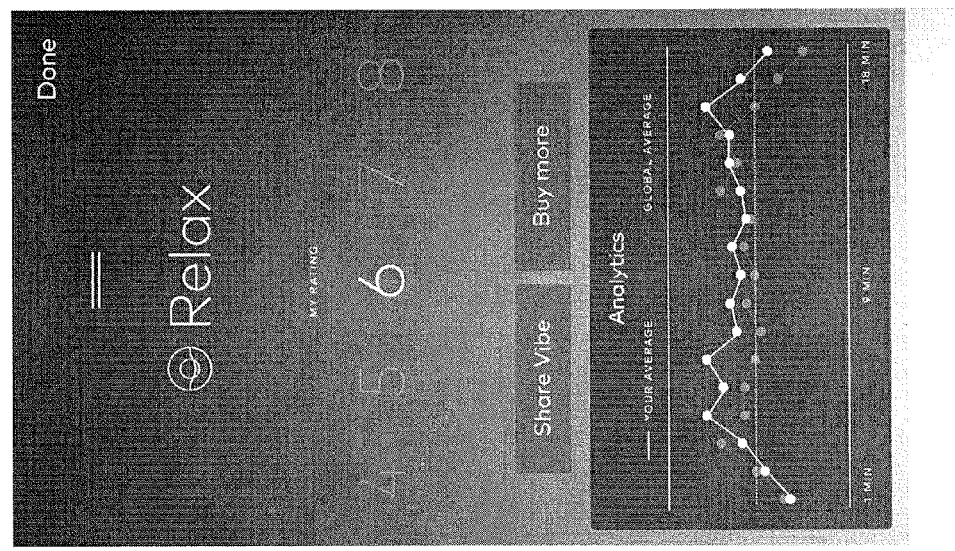
FIG. 11A illustrates a user interface that allows the user to select a ranking and share the waveform ensemble (or rating thereof).
Figure 11D:
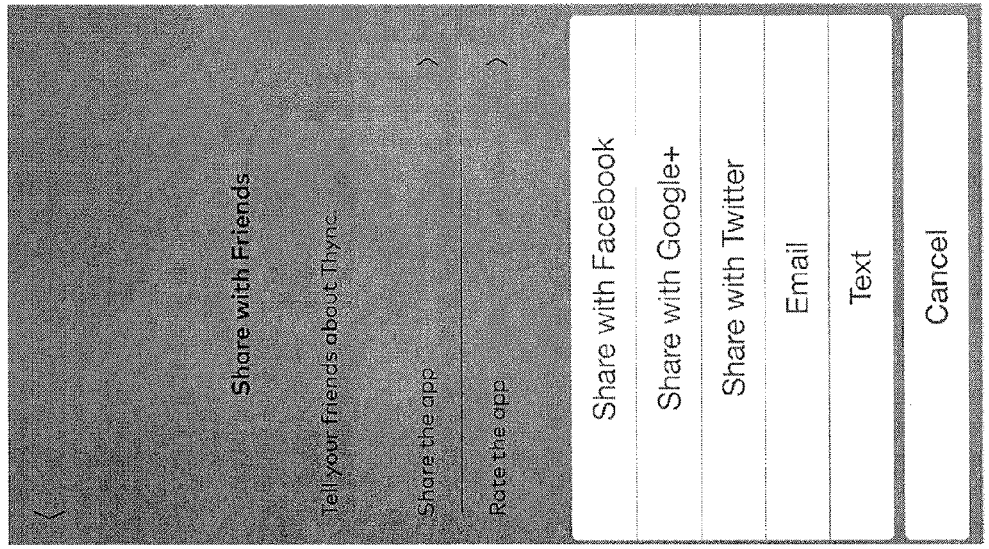
FIG. 11D illustrates yet another example of a user interface that allows the user to share his/her experience with friends via Facebook, Google+, Twitter, email, or text.
Figure 11C:
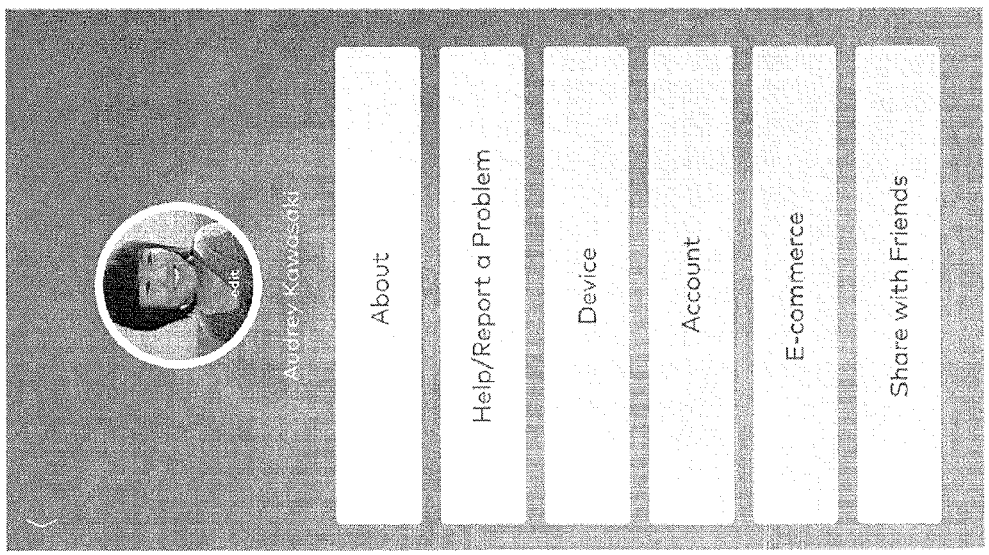
FIG. 11C illustrates another example of a user interface that allows the user to share his/her experience with friends.

In some embodiments, the user device may allow the user to provide rating/tagging/ranking/scoring/feedback on the waveform ensemble. For example, FIG. 11A illustrates a user interface that allows the user to select a rating and share the waveform ensemble. In some embodiments, the user device may also create a community where a group of users may share the waveform ensembles, view the rankings from other users, and communicate their experiences. For example, FIG. 11B illustrates a user interface that allows the user to submit a response. FIG. 11C illustrates another example of a user interface that allows the user to share his/her experience including homebrewed (e.g., personally designed or adapted) waveform ensembles with friends. FIG. 11D illustrates yet another example of a user interface that allows the user to share his/her experience with friends, e.g. via Facebook, Google+, Twitter, email, or text. In some embodiments, the user device allows the user to contact support, report a problem, obtain knowledge about the neurostimulation, and access a quick start guide as illustrated in FIGS. 11B, 11C and 11D.

As used herein, when the 'user device' (or user computing device) is performing a function or operation, it should be understood that this may be achieved by software (e.g., an application), hardware, firmware, or some combination thereof, configuring and controlling the operation of the user device.

Figures 11E, 11F:
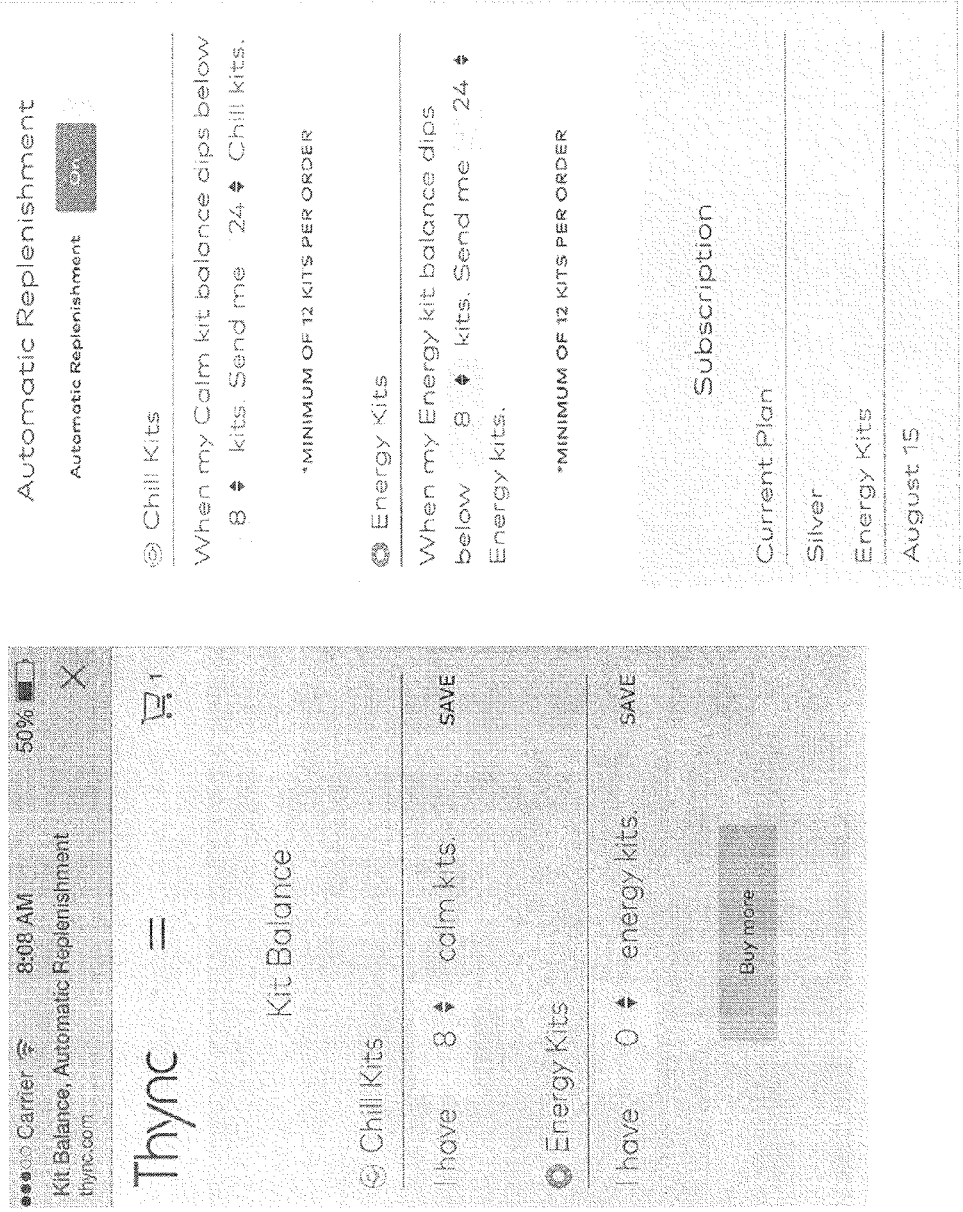
FIG. 11E illustrates a user interface that displays the user's estimated supply of electrodes and allows the user to adjust this estimate.
FIG. 11F illustrates a user interface that provides the user a subscription service that automatically ships the electrodes.

In some embodiments, the user device may provide the user a marketplace for buying, selling, renting, borrowing, or otherwise acquiring ensemble waveforms or making an ensemble waveform available for sale (rent, lending, etc.). The user device may also provide the user a marketplace allowing the user to purchase more electrode kits through the user device as illustrated in FIG. 11A. In some embodiments, the user device may monitor the usage of electrodes by the user as illustrated in FIG. 11E. The user device may keep a record of the number and amount of electrodes the user purchased, and keep track of the usage of the electrodes. Whenever the user runs a TES neurostimulation session, the user device may detect the type of electrode the user is applying and update the number of electrodes left after the neurostimulation session. In some embodiments, the user device may estimate the electrode need and ship automatically to the user. In some embodiments, the user device may allow the user to choose a subscription service that will ship the electrodes automatically when the electrodes count is below a user specified level. For example, FIG. 11F illustrates a user interface that provides the user a subscription service that automatically ships the electrodes. In some embodiments, the user device may allow the user to specify the level of the electrodes to trigger the automatic shipping. The user device may also allow the user to specify the amount of electrodes to be shipped automatically in some embodiments.

FIG. 12 illustrates a flow chart for user control of a neurostimulator by controlling a waveform ensemble in accordance with one embodiment of the invention. In some embodiments, a method for controlling a waveform ensemble may include running and controlling the waveform ensemble from a user computing device configured with an application, such that the application is stored on a non-transitory computer readable medium and executable by the computing device, during a transdermal electrical stimulation session. The method may include allowing the user to select a subset of cognitive states on the user computing device. The method may include presenting a plurality of waveform ensembles to the user with a user device S100. The method may include allowing the user to select a waveform ensemble on the user computing device S110. The method may include allowing the user device to communicate with the neurostimulator and to transmit the parameter(s) of the user selected waveform ensemble to the neurostimulator S120. Further, the method may include modulating the waveform ensemble during the transdermal electrical stimulation session. For example, the method may include allowing the user to control the waveform ensemble using at least one interactive component on a user interface on the user computing device during the neurostimulation session S130. For example, the method may include allowing the user to adjust the perceived intensity of the waveform ensemble during the neurostimulation session. In some embodiments, the method may include allowing the user to share at least one element of the waveform ensemble with neuromodulator users S140.

In some embodiments, the method may optionally include allowing the user to trigger a phosphene or an intensifier or other pre-determined signals during a transdermal electrical stimulation session. In some embodiments, the method may include allowing the user to share at least one of the elements of the waveform ensemble via a social networking website, through email, or any other type of communication framework. In some embodiments, a user may share an element and/or nested waveform before, during, and/or after a transdermal electrical stimulation session. In some embodiments, the user device may generate a user interface, dialogue box, or pop-up window to prompt the user to share an element of the waveform ensemble. In some embodiments, other friends and/or users may send a user a request through email, text, social networking website, or another type of user interface for his/her element and/or nested waveform.

In some embodiments, the method may include a user delivering the waveform ensemble parameters to a neuromodulation device controller. In some embodiments, delivering may include saving, exporting, emailing, texting, uploading, downloading, or any other type of strategy and/or system for sending an electronic file to the same or another location or virtual location. In some embodiments, the waveform ensemble may be delivered to the user computing device including a laptop, desktop computer, mobile phone, tablet, or any other type of computing device.

In some embodiments, the method may include allowing the user to control the waveform ensemble using at least one interactive component on the user interface on a first computing device or a second computing device. In some embodiments, controlling may include adding, removing, reordering, resequencing, modifying, changing, altering, exchanging, and/or swapping elements and/or parameters. In some embodiments, a user may use a web-enabled user interface or any other type of user interface to control and/or modify a transdermal electrical stimulation session. In some embodiments, the waveform ensemble may be downloaded to the user computing device, as described above.

The systems, devices, and methods of the preferred embodiments and variations thereof can be embodied and/or implemented at least in part as a machine configured to receive a computer-readable medium storing computer-readable instructions. The instructions are preferably executed by computer-executable components preferably integrated with the system including the computing device configured with software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of modifying a user's cognitive state using a neurostimulator worn on the user's body, the method comprising:

allowing the user to select a waveform ensemble from a plurality of different waveform ensembles on a user device, wherein each waveform ensemble comprises a set of waveform parameters specifying current intensity, frequency, and duty cycle;

transmitting the selected waveform ensemble, an identifier of the selected waveform ensemble, or the set of waveform parameters corresponding to the selected waveform ensemble to the neurostimulator for application of the selected waveform ensemble by the neurostimulator worn on the user;

displaying on the user device, a representation of an intensity of the selected waveform ensemble over a duration of application of the selected waveform ensemble and a display of a user-adjusted intensity relative to the intensity of the selected waveform ensemble; and allowing the user to adjust the intensity of the selected waveform ensemble with the user device during application of the selected waveform ensemble.

2. The method of claim 1, wherein allowing the user to select comprises allowing the user to select from a subset of waveform ensembles that are configured to evoke a type of cognitive state.

3. The method of claim 1, further comprising receiving in the user device, a signal from the neurostimulator indicating that an electrode has been attached to the neurostimulator.

4. The method of claim 1, further comprising displaying a representation of a maximum intensity of the selected waveform ensemble to be delivered by the neurostimulator on the user device.

5. The method of claim 1, further comprising allowing the user to rank or score a waveform ensemble in the plurality of waveform ensembles and storing, transmitting, or storing and transmitting the user rank or score.

6. The method of claim 1, further comprising allowing the user to download a new waveform ensemble to the user device.

7. The method of claim 1, further comprising displaying a rank or score for the selected waveform ensemble.

8. The method of claim 1, further comprising allowing the user to trigger, from the user device, transmission of an interrupt signal to the neurostimulator during the application of the selected waveform ensemble, wherein the interrupt signal temporarily modifies the application of the selected waveform ensemble for a predefined timer period.

9. The method of claim 1, further comprising allowing the user to trigger, from the user device, transmission of an interrupt signal to the neurostimulator during the application of the selected waveform ensemble, wherein the interrupt signal temporarily modifies the application of the selected waveform ensemble for a predefined timer period, and wherein the interrupt signal is configured to evoke a phosphene.

10. The method of claim 1, further comprising allowing the user to trigger, from the user device, transmission of an interrupt signal to the neurostimulator during the application of the selected waveform ensemble, wherein the interrupt signal is configured to transiently decrease and then increase or transiently increase and then decrease the intensity of the selected waveform ensemble.

11. The method of claim 1, further comprising allowing the user to confirm the position of the neurostimulator, an electrode coupled to the neurostimulator, or the neurostimulator and an electrode by displaying in approximate real-time, images from a camera on the user device so that the user may view an image of the user's body.

12. A method of modifying a user's cognitive state using a neurostimulator worn on the user's body, the method comprising:

presenting a plurality of waveform ensembles to a user with a hand-held user device, wherein the plurality of waveform ensembles includes different waveform ensembles and wherein at least some of the waveform ensembles comprise multiple sequentially arranged sets of waveform parameters wherein each set specifies a current intensity, a frequency, and a duty cycle;

allowing the user to select a waveform ensemble from the plurality of different waveform ensembles on a user device;

transmitting the selected waveform ensemble, an identifier of the selected waveform ensemble, or the set of waveform parameters corresponding to the selected waveform ensemble to the neurostimulator for application of the selected waveform ensemble by the neurostimulator worn on the user's body;

applying the selected waveform ensemble from the neurostimulator to modify the user's cognitive state;

displaying on the user device, a representation of an intensity of the selected waveform ensemble and a display of a user-adjusted intensity relative to the intensity of the selected waveform ensemble; and allowing the user to adjust the intensity of the selected waveform ensemble with the hand-held user device during application of the selected waveform ensemble.

13. The method of claim 12, wherein allowing the user to select comprises allowing the user to select from a subset of waveform ensembles that are configured to evoke a type of cognitive state.

14. The method of claim 12, further comprising receiving in the user device, a signal from a neurostimulator indicating that an electrode has been attached to the neurostimulator.

15. The method of claim 12, further comprising displaying a representation of a maximum intensity of the selected waveform ensemble to be applied by the neurostimulator on the hand-held user device.

16. The method of claim 12, further comprising displaying a rank or score for the selected waveform ensemble.

17. The method of claim 12, further comprising allowing the user to trigger, from the user device, transmission of an interrupt signal to the neurostimulator during the application of the selected waveform ensemble, wherein the interrupt signal temporarily modifies the application of the selected waveform ensemble for a predefined timer period.

18. The method of claim 12, further comprising allowing the user to trigger, from the user device, transmission of an interrupt signal to the neurostimulator during the application of the selected waveform ensemble, wherein the interrupt signal temporarily modifies the application of the selected waveform ensemble for a predefined timer period, and wherein the interrupt signal is configured to evoke a phosphene.

19. The method of claim 12, wherein presenting the plurality of waveform ensembles comprises indicating ranking or scoring information for individual waveform ensembles in the plurality of waveform ensembles based on ranks or scores made by other users or by the user.

20. A method of modifying a user's cognitive state using a neurostimulator worn on the user's body, the method comprising:

allowing the user to select a waveform ensemble from a plurality of different waveform ensembles on a user device, wherein each waveform ensemble comprises a set of waveform parameters specifying current intensity, frequency, and duty cycle;

transmitting the selected waveform ensemble, an identifier of the selected waveform ensemble, or the set of waveform parameters corresponding to the selected waveform ensemble to the neurostimulator for application of the selected waveform ensemble by the neurostimulator worn on the user;

displaying on the user device, a representation of an intensity of the selected waveform ensemble to be delivered by the neurostimulator over a duration of application of the selected waveform ensemble;

allowing the user to adjust the applied intensity of the selected waveform ensemble as the selected waveform ensemble is applied to the user by the neurostimulator; and displaying, on the representation of the intensity of the selected waveform ensemble, a representation of the user-adjusted intensity relative to the intensity of the selected waveform ensemble.

* * * * *